United States Patent [19]
Apperson et al.

[11] Patent Number: 5,146,092
[45] Date of Patent: Sep. 8, 1992

[54] GAS ANALYSIS TRANSDUCERS WITH ELECTROMAGNETIC ENERGY DETECTOR UNITS

[75] Inventors: Jerry R. Apperson; Daniel W. Knodle, both of Seattle; Lawrence L. Labuda, Issaquah; James T. Russell, Bellevue; Gary M. Bang, Edmonds, all of Wash.

[73] Assignee: NTC Technology, Inc., Wilmington, Del.

[21] Appl. No.: 687,012

[22] Filed: Apr. 16, 1991

Related U.S. Application Data

[62] Division of Ser. No. 528,059, May 23, 1990.

[51] Int. Cl.⁵ .......................................... G01N 21/61
[52] U.S. Cl. .................................... 250/343; 250/345; 250/352; 128/719
[58] Field of Search ............... 250/237, 343, 345, 352; 128/719

[56] References Cited

U.S. PATENT DOCUMENTS

| | | | |
|---|---|---|---|
| 2,737,591 | 3/1956 | Wright et al. | |
| 3,004,664 | 10/1961 | Dreyfus. | |
| 3,287,556 | 11/1966 | Good. | |
| 3,306,156 | 2/1967 | Glasser et al. | 250/373 |
| 3,539,804 | 11/1970 | Billetdeaux et al. | 250/343 |
| 3,806,727 | 4/1974 | Leonard et al. | 250/345 |
| 3,811,776 | 5/1974 | Blau, Jr. | 250/343 |
| 3,821,553 | 6/1974 | French | 250/345 |
| 3,822,098 | 7/1974 | Rudder et al. | 250/339 |
| 3,860,344 | 1/1975 | Garfunkel | 250/345 |
| 3,860,818 | 1/1975 | Staldor et al. | 250/343 |
| 3,916,195 | 10/1975 | Burch et al. | 250/345 |
| 4,394,572 | 7/1983 | Wilber | 250/239 |
| 4,410,273 | 10/1983 | Mantz et al. | 250/339 |
| 4,468,561 | 8/1984 | Speeter | 250/339 |
| 4,536,090 | 8/1985 | Schmidt et al. | 250/339 |

*Primary Examiner*—Carolyn E. Fields
*Attorney, Agent, or Firm*—Hughes & Multer

[57] ABSTRACT

A transducer for nondispersive infrared gas analysis has heaters for the data and reference detectors to maintain the detectors at a selected temperature. A heater is also provided to heat the casing of an airway adapter associated with the transducer to a temperature high enough to keep condensation from forming. The detector unit is surrounded and electrostatically shielded by a boxlike component with barndoor extensions which are closed to shield the installed detector unit at that end of the shield through which the detector unit is installed. The detector unit, electrostatic shield, and a circuit board which carries power supply and preamplifier circuits are installed in the transducer housing which has separate end closures sealed thereto with a through fastener and internal guides for locating the shielded detector unit in the housing.

24 Claims, 16 Drawing Sheets

GAS ANALYSIS TRANSDUCERS WITH ELECTROMAGNETIC ENERGY DETECTOR UNITS

RELATION TO COPENDING APPLICATION

The present application is a division of application No. 07/528,059 filed May 23, 1990.

TECHNICAL FIELD OF THE INVENTION

The present invention relates to detectors and, more specifically, to novel, improved, infrared radiation detector units.

BACKGROUND OF THE INVENTION

U.S. Pat. Nos. 4,859,858 and 4,859,859, both entitled GAS ANALYZERS, were issued to Knodle et al. on Aug. 22, 1989. Both patents disclose state-of-the art apparatus for outputting a signal indicative of the concentration of a designated gas in a sample being monitored by the apparatus.

The gas analyzers disclosed in the '858 and '859 patents are of the non-dispersive type. They operate on the premise that the concentration of a designated gas can be measured by: (1) passing a beam of infrared radiation through the gas, and (2) then ascertaining the attenuated level of the energy in a narrow band absorbable by the designated gas. This is done with a detector capable of generating a concentration proportional electrical output signal.

One important application of the invention at the present time is in capnometers for monitoring the level of carbon dioxide in the breath of a medical patient. This is typically done during a surgical procedure as an indication to the anesthesiologist of the patient's condition, for example. As the patient's wellbeing, and even his life, is at stake, it is of paramount importance that the carbon dioxide concentration be measured with great accuracy.

In a typical instrument or system employing non-dispersive infrared radiation to measure gas concentration, including those disclosed in the '858 and '859 patents, the infrared radiation is emitted from a source and focused by a mirror on the gases being analyzed. After passing through the body of gases, the beam of infrared radiation passes through a filter. That filter absorbs all of the radiation except for that in a narrow band centered on a frequency which is absorbed by the gas of concern. This narrow band of radiation is transmitted to a detector which is capable of producing an electrical output signal proportional in magnitude to the magnitude of the infrared radiation impinging upon it. Thus, the radiation in the band passed by the filter is attenuated to an extent which is proportional to the concentration of the designated gas. The strength of the signal generated by the detector is consequently inversely proportional to the concentration of the designated gas and can be inverted to provide a signal indicative of that concentration.

While a non-dispersive analyzer must be tailored to the specific gas of interest, it is typically small, relatively cheap, and rugged enough to be used in medical and other demanding environments.

Most non-dispersive infrared gas analyzers use a ratioing scheme to eliminate errors attributable to drifts in the infrared source and other parts of the system and transmission losses. Two methods are common.

1. An optical chopper is used with a single detector. The chopper contains a reference cell or filter, and the detector signal alternates between that reference cell and the gas to be measured. A ratio is taken of these two signals.

2. Two detectors are located next to each other, and each is illuminated by one-half of the infrared beam. A ratio is taken of the two detector outputs. The reference channel is presumed to be responsive to any changes in the detected energy that are not due to the absorption of the designated gas, and the changes are presumed to be the same in both the reference and data channels.

A major drawback of the optical chopper technique is that it requires a device with moving parts to implement it. Such devices tend to be expensive, bulky, and fragile and to require frequent calibration.

Another difficulty, common to both schemes, is that the ratioed signals are different in time in the first case and different in space in the second. These differences can produce a false signal from the detector if there are time variations in the first case or spatial variations in the second case.

Also, any motion in the system can cause time and spatial variations in the infrared radiation beam. At best, this can require frequent recalibration. Recalibration is time consuming and expensive and takes the unit or system out of operation which may be unacceptable — for example, a major surgical procedure cannot be interrupted simply to recalibrate an instrument.

Dispersive infrared analysis is also utilized to measure the concentration of a designated gas in a stream or other sample being analyzed. In this approach, a broad band of energy is transmitted through the gas, then through a dispersive element, typically a prism or a diffraction grating. The dispersive element spreads out the energy according to wavelength. The intensity of the energy will vary across that space depending on the absorption characteristics of the gas under analysis.

A detector scans through a large range of wavelengths, thereby recording intensity (i.e., absorption of the gas) as a function of wavelength. A manual or electronic examination of this recording will identify the gas or gases that may h=present. The detector can also be fixed in space, thus recording the intensity of a particular wavelength (and gas) of interest.

The dispersive type of gas analyzer is especially useful where an unknown gas may be present because a very large range of wavelengths can be covered. It is also useful where there are several gases present.

The dispersive analyzer is flexible and can be very accurate, but it is expensive and bulky. It is most often found in a laboratory, and it is not at all suitable for applications such as those medical applications in which the entire emitter/detector system may have to be suspended in the plumbing between a patient and a mechanical ventilator, for example.

SUMMARY OF THE INVENTION

There have now been invented, and disclosed herein, certain new and novel infrared radiation detector units which, when employed in the non-dispersive measurement of a designated gas, make it possible to do this more accurately than is believed to have heretofore been possible by way of that approach. This is a significant advantage, especially in medical and other applications where a high degree of accuracy is of the utmost importance. At the same time, and unlike dispersive-type analyzers, these novel detector units and systems are compact and rugged enough for the most demanding applications and are relatively inexpensive to produce.

Increased accuracy is achieved, in accord with the principles of the present invention, by a novel beam splitter which divides the energy over the entire compass of a beam passed through gases being analyzed into moieties in which the energy is of wavelengths that are respectively shorter and longer than a designated wavelength. The energy in these moieties is transmitted through appropriate bandpass filters to data and reference detectors of like dimensions which are positioned in mirror image relationship to the beam splitter. Consequently, both detectors receive energy of appropriate wavelengths from all parts of the beam. This eliminates the inaccuracies which occur in side-by-side and other detector systems in which: (1) the image of the beam falling on the detectors is different in space because the data and reference detectors are not spatially coincident, and/or (2) different in time because the beam reaches the data and reference detectors through first one and then the other of the bandpass filters in front of those detectors.

A novel, monolithic, isothermal mount supports the beam splitter and the reference and data detectors with the precision required for optimal accuracy. Light traps associated with the mount keep extraneous energy from reaching the detectors, providing a further increase in accuracy.

Associated with the system for maintaining the data and reference detectors at the wanted temperature is an onboard power supply. The power supply output voltage is used to bias the detectors; and, because the output is precisely regulated, this is done essentially without the inaccuracies in the outputs from the data and reference detectors that would occur if the biasing voltage fluctuated. Lead selenide-type detectors are preferred because of their sensitivity and consequent capability for accurately reflecting the magnitude of the infrared radiation falling on them. However, this means that they are equally sensitive to variations in temperature. Therefore, even minor fluctuations in the detector temperature and minor differences between the temperatures of the data and reference detectors can markedly affect accuracy.

A sensor/heater system promotes accuracy by heating the isothermal support in a manner that keeps the two detectors precisely at a selected temperature, typically with a variation $\leq 0.01°$ C. The support is fabricated from a heat conductive material and so configured as to reduce to this very small value the temperature difference between the data and reference detectors.

At the same time, the novel, monolithic detector supports and other hereinafter discussed features of the devices make them rugged, but still compact.

Also incorporated in the detector unit are a pair of electronic amplifiers. These increase the outputs from the data and reference detectors to levels at which they can be transmitted without excessive noise to a signal processor. The signal processor converts the detector outputs to a signal reflecting the concentration of the selected gas in the stream or other sample being analyzed.

Typically, detector units of the character disclosed herein are employed in environments in which electrical noise is prevalent. A novel electrostatic shield effectively isolates the data and reference detectors and associated circuitry from the adverse effects of EMI and other radiations in the ambient surroundings.

A novel casing houses the electrostatic shield and the detectors and other electrical and optical components of the detector unit and keeps foreign matter from reaching those components. Guide systems in the casing and in the electrostatic shield facilitate the assembly of the unit and the electrical connection of the electrostatic shield to the components shielded by that device.

The casing in which the detector unit is housed may be one component of a transducer which also includes a source with components for: emitting electromagnetic energy, focusing that energy into a beam, and propagating the beam through the gases being analyzed. In applications of the invention which are of particular interest at the present time, these transducers are used with an airway adapter to measure the concentration of a gas such as carbon dioxide flowing through the adapter.

These airway adapters are typically disposable, and optical characteristics may vary from one adapter to the next. This, however, is inconsequential, and interchangeability is provided, when a detector unit of the character disclosed herein is employed in the transducer. Because both the data and reference detectors of such units react to the energy over the same compass of the attenuated beam, optical variations — and others including drift, foreign substances in the optical path, etc. — affect both detectors in the same manner and to the same extent. Therefore, anomalies are canceled out when the data and reference detector outputs are ratioed. This also means that the frequent recalibration required in other non-dispersive, dual detector systems is unnecessary or, at worst, minimized.

Preferably, a second system independent of that utilized to control detector temperatures is employed to keep the casing of the airway adapter at an elevated temperature (preferably in the 42°–45° C. range). This is high enough to keep moisture from condensing on those windows incorporated in the adapter to pass the radiant energy into that device and, after it has passed through the gas being analyzed, to the detector system. This approach to eliminating the problems that condensation might cause has the important advantage that heating the airway adapter has no effect on the power supplied to the data and reference detector heaters. Consequently, the fluctuations in the detector heater power supply that would occur as the casing heats up if the casing heater and detector heater circuits were tied together are eliminated. So are the unwanted changes in detector temperature that would be caused by such fluctuations.

THE PRIOR ART

A number of U.S. patents disclose optical systems which: (1) have detectors and beam splitters, and (2) are intended for purposes at least generally comparable to those disclosed herein. They are:

| U.S. Pat. No. | Patentee(s) | Issue Date |
|---|---|---|
| 2,737,591 | Wright et al. | 6 March 1956 |
| 3,004,664 | Dreyfus | 17 October 1961 |
| 3,287,556 | Good | 22 November 1966 |
| 3,811,776 | Blau, Jr. | 21 May 1974 |
| 3,821,553 | French | 28 June 1974 |
| 3,916,195 | Burch et al. | 28 October 1975 |
| 4,410,273 | Mantz et al. | 18 October 1983 |
| 4,468,561 | Speeter | 28 August 1984 |

-continued

| U.S. Pat. No. | Patentee(s) | Issue Date |
| --- | --- | --- |
| 4,536,090 | Schmidt et al. | 20 August 1985 |

None of the foregoing patents are concerned with a detector unit or system which the highly desirable attribute of interchangeability.

Nor, with the possible exception of Good, do the patented systems make use of a beam splitter which is capable of resolving a beam over its entire compass into energy which is respectively above and below a selected wavelength. And, even Good only discloses that this can be done with his beam splitter if the inputted energy is coherent. This requirement for laser generated energy would make the Good system too complicated, bulky, and expensive for at least many of the applications for which the novel detector units and systems disclosed herein are so well suited. Furthermore, Good has not disclosed how this patented system could be constructed to meet the FDA (Food and Drug Administration) requirements for Class III lasers. Absent FDA approval, the system would of course have the disadvantage of being of no significant practical value.

OBJECTS OF THE INVENTION

From the foregoing, it will be apparent to the reader that one important and primary object of the present invention resides in the provision of novel units and systems for detecting energy in the infrared portion of the electromagnetic spectrum.

Other also important but more specific objects of the invention reside in the provision of systems as characterized in the preceding object:

which are particularly useful in non-dispersive type gas analyzers to generate a reference signal and a signal indicative of the concentration of a selected gas in a simple being analyzed;

which are compact and rugged and therefore particularly well suited for field use in medical and other demanding applications;

which do not require the frequent recalibration heretofore needed in non-dispersive systems to compensate for accumulations of energy absorbing foreign substances on optical components of the system;

which are extremely accurate due to a novel arrangement for precisely aligning the optical components of the system;

in which accuracy is promoted by a novel arrangement for keeping the detectors of the system — a reference detector and a data detector — at the same, selected temperature:

which have a beam splitter that directs incoming electromagnetic energy to the reference and data detectors and differs from conventional beam splitters in that all of the incoming energy in a band absorbed by a selected gas of interest is directed to the data detector and in that the remainder of the incoming energy over the same compass of the beam is directed to the reference detector so that both detectors respond to the same compass of the incoming beam, thereby increasing the accuracy of the system;

in which accuracy is promoted by a novel system for electrostatically shielding the operating components of the system;

which have integral circuitry for amplifying the signals outputted from the reference and data detectors and thereby reducing the effect of noise on those signals;

which have traps that keep extraneous electromagnetic energy from reaching the reference and data detectors;

which are easily assembled in a transducer head that also has an infrared radiation source and in a manner that facilitates the making of subsequent electrical connections among the assembled components;

which have a novel housing construction that isolates optical components from the surrounding environs to prevent contamination, yet allows electromagnetic energy to reach those components without interference;

which can be used in a variety of applications and to measure the concentrations of many different gases; and which, in conjunction with the foregoing object, can advantageously be employed in conjunction with an airway adapter to accurately measure the concentration of a designated gas flowing through the adapter.

Objects related to the one just expressed include the provision of detector units and systems:

which remain accurate as another airway adapter is substituted for the preceding one even though the optical characteristics of those adapters — including dimensions — may vary;

which have associated therewith a system for heating the airway adapter casing to a temperature high enough to keep moisture from forming on the casing and interfering with the accuracy afforded by the detector system;

in which, in conjunction with the preceding object, independently controlled systems are employed to heat: (a) the airway adapter casing, and (b) the data and reference detectors so that the heating of the airway adapter casing does not introduce inaccuracies into the signals outputted by the detectors.

Other important objects and features and additional advantages of the invention will be apparent to the reader from the foregoing and the appended claims and as the ensuing description and discussion proceeds in conjunction with the accompanying drawing.

DETAILED DESCRIPTION OF THE INVENTION

Figure 4:
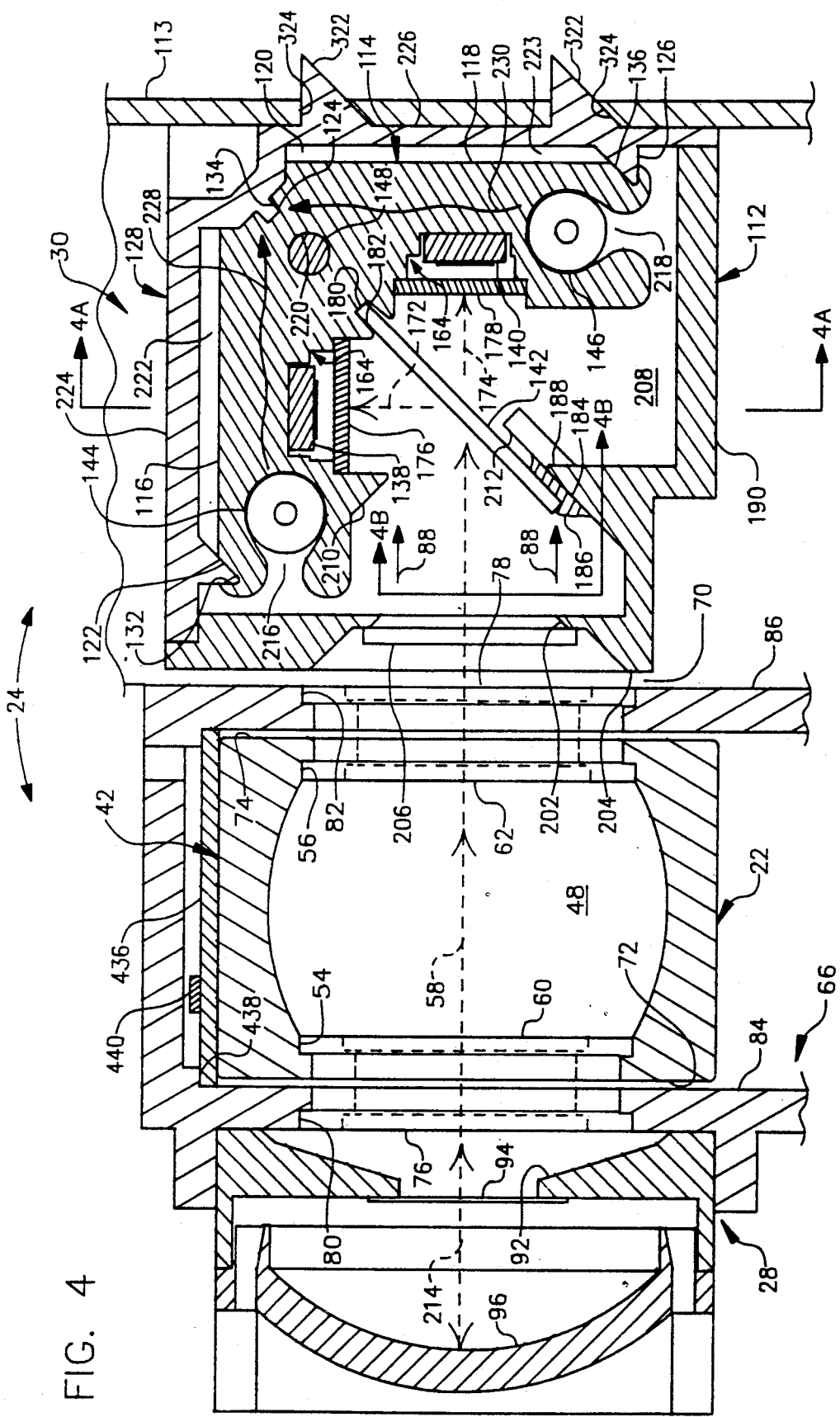
FIG. 4 is a section through, and depicts, a detector-incorporating optical system of the airway adapter/transducer assembly.

The principles of the present invention can be employed to particular advantage in transducers for outputting: (a) a signal proportional in magnitude to the concentration of carbon dioxide flowing through an airway adapter in a patient-to-mechanical ventilator circuit, and (b) a reference signal. These signals can be ratioed in the manner disclosed in above-incorporated U.S. Pat. Nos. 4,859,858 and 4,859,859 to provide a third signal accurately and dynamically representing the concentration of the carbon dioxide flowing through the airway adapter. A representative and preferred airway adapter and a complementary transducer constructed in accord with, and embodying, the principles of the present invention are shown in FIGS. 1, 2, and 4 and respectively identified by reference characters 22 and 24.

Figure 1:
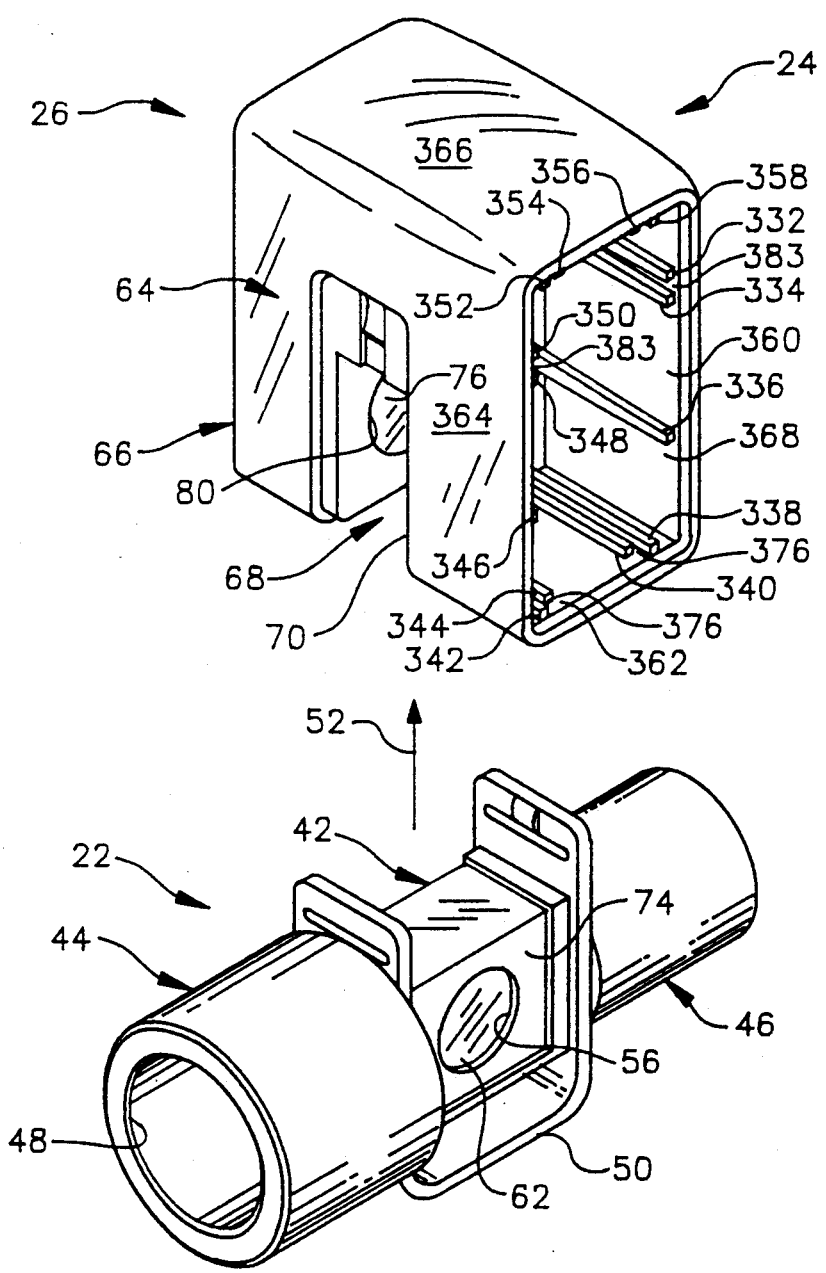
FIG. 1 is an exploded view of: (a) an airway adapter which provides a particularized flow path for a gas being analyzed, and (b) a transducer which outputs a signal indicative of the concentration of the designated gas in the mixture and a reference signal; that transducer includes a detector unit constructed in accord with the principles of the present invention.
Figure 2:
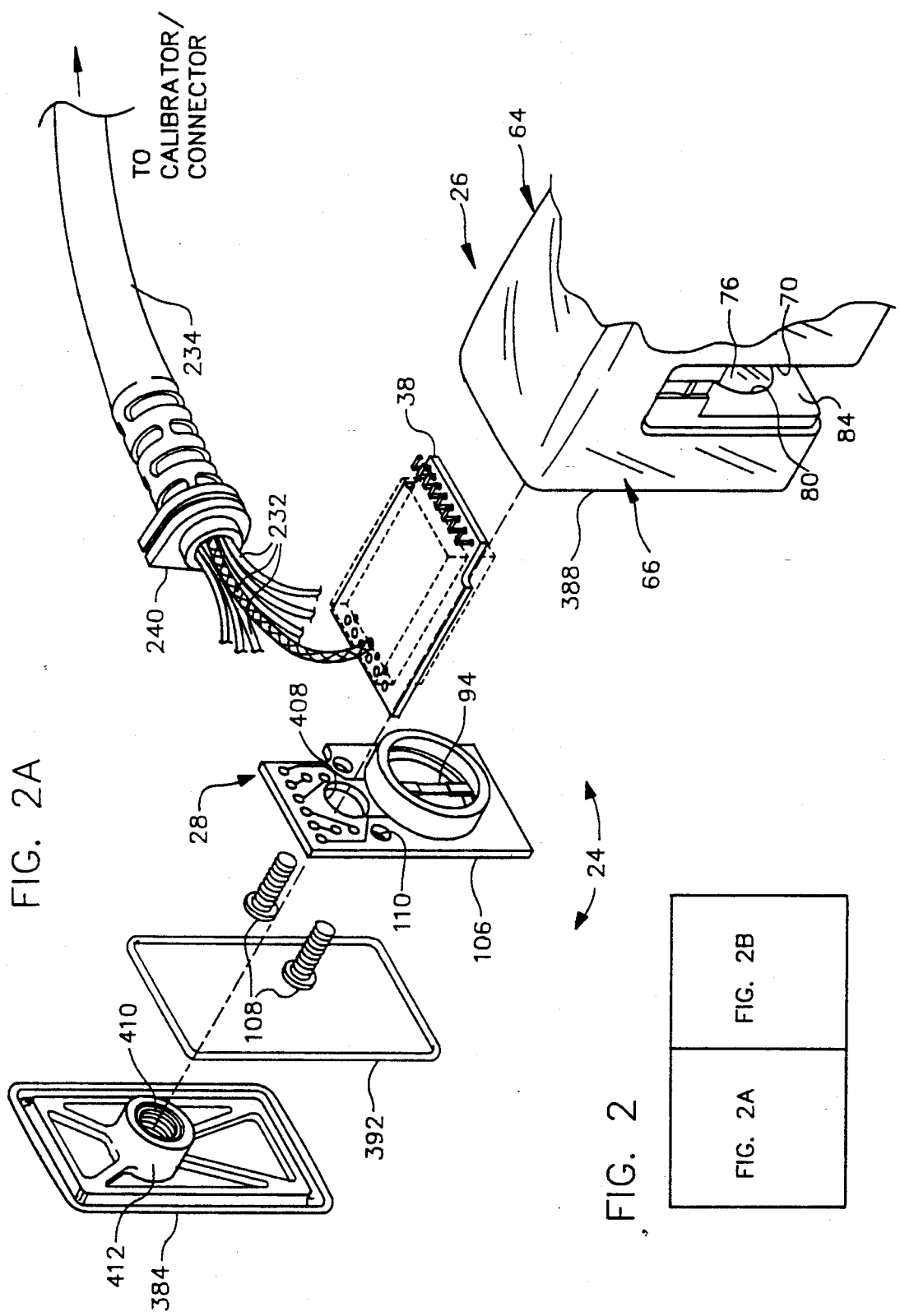
FIG. 2 shows the relationship between FIGS. 2A and 2B which, together, constitute an exploded view of the transducer.
Figure 3:
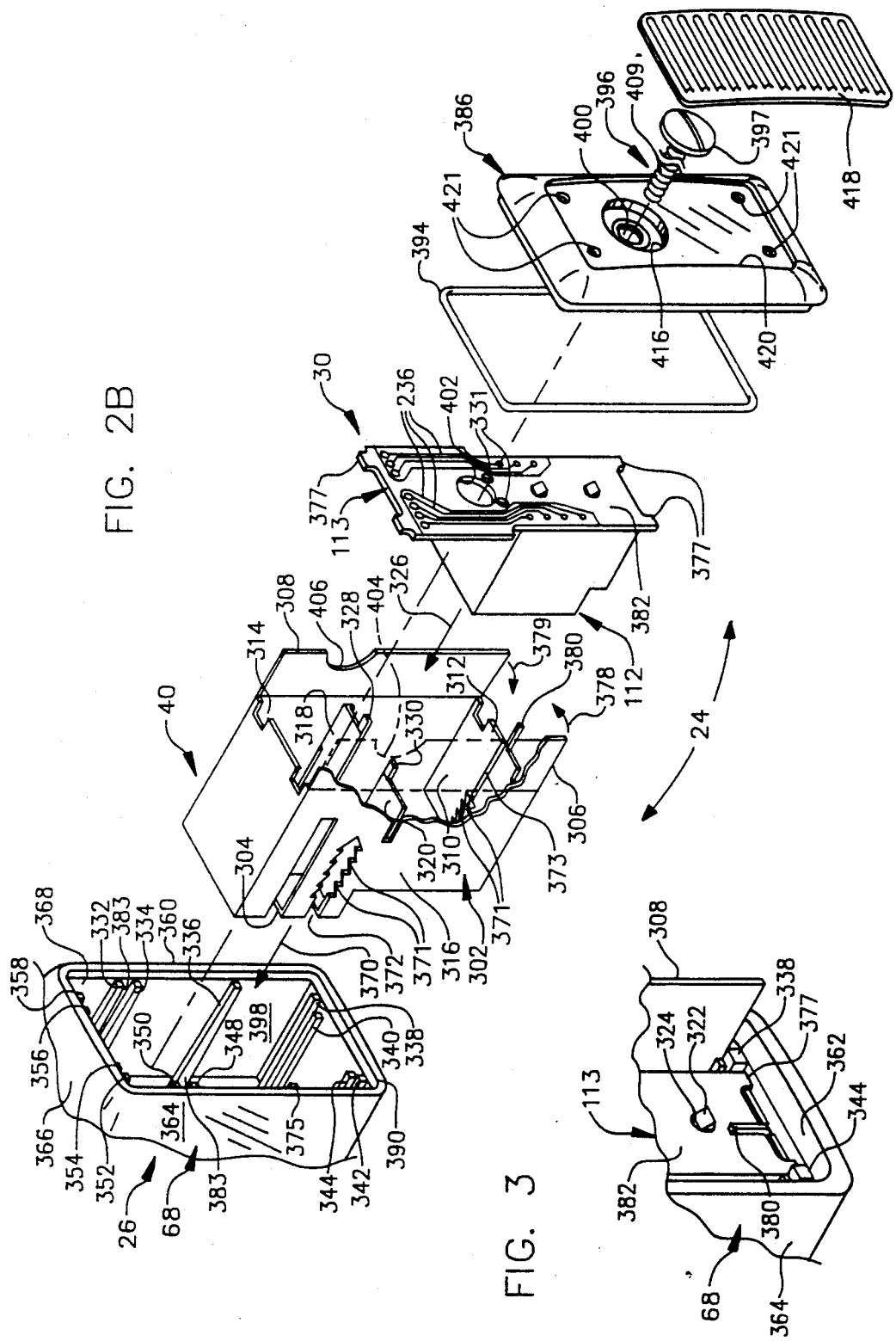
FIG. 3 is a fragmentary view of the transducer, partially assembled and showing the manner in which a printed circuit board in the detector unit is connected up to an electrostatic shield in the transducer.
Figure 4A:
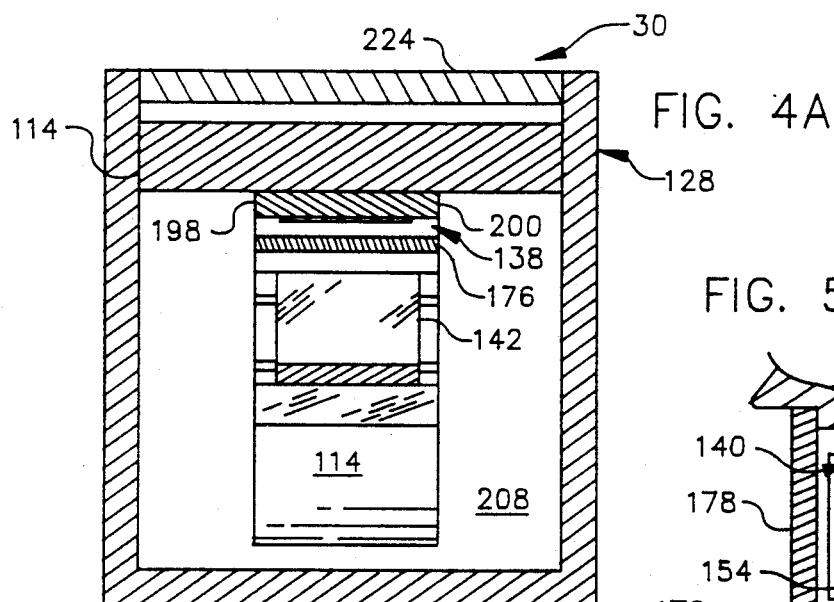
FIG. 4A is a fragmentary view of the optical system looking in the direction of arrows 4A—4A in FIG. 4.
Figure 6:
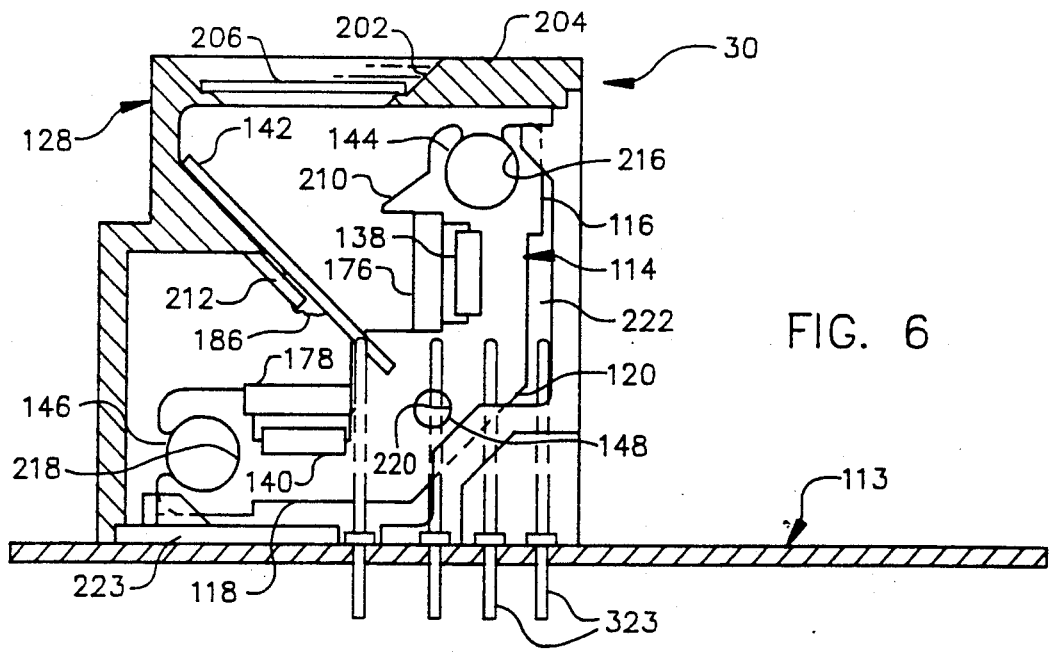
FIG. 6 is a longitudinal section through the detector unit.
Figure 4B:
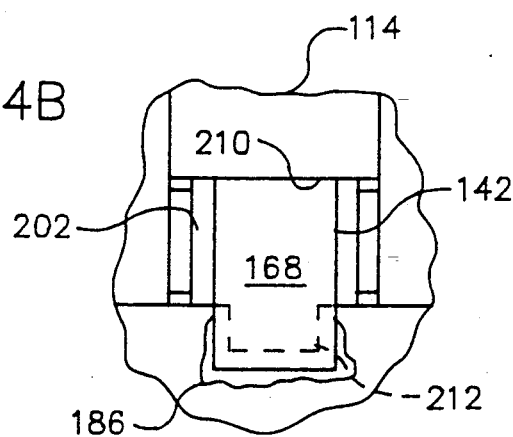
FIG. 4B is a fragmentary view of the detector unit taken along line 4B—4B of FIG. 4 to facilitate an understanding of the manner in which certain light traps incorporated in the detector unit function.

Referring now to the drawing, FIG. 1 depicts the polymeric housing 26 of transducer 24. This transducer also includes: (a) an electromagnetic energy emitter or source unit 28 (FIGS. 2A and 4); (b) a detector unit 30 (FIGS. 2B, 4, and 6); (c) a detector unit power supply 32 (FIGS. 9 and 12) and data and reference detector amplifiers 34 and 36 (FIGS. 9, 10, and 11) mounted on a printed circuit board 38 (PCB) (FIG. 2); and (d) an electrostatic shield 40 (FIG. 4B).

The illustrated airway adapter 22 is designed for connection between an endotracheal tube inserted in a patient's trachea and the plumbing of a mechanical ventilator, and transducer 24 is in this instance employed to measure the expired carbon dioxide level of a medical patient.

The particular airway adapter 22 illustrated in FIG. 1 is not, by itself, part of the present invention. Consequently, it will be described herein only to the extent necessary for an understanding of the present invention.

Referring then to FIGS. 1 and 4, airway adapter 22 is a one-piece unit typically molded from Valox polyester or a comparable polymer. Airway adapter 22 has a general parallelepipedal center section 42 and two cylindrical end sections 44 and 46 with a sampling passage 48 extending from end-to-end through the adapter. End sections 44 and 46 are axially aligned with center section 42.

The central section 42 of airway adapter 22 provides a seat for transducer 24. An integral, U-shaped component 50 positively locates transducer 24 endwise of the adapter and, also, in that transverse direction indicated by arrow 52 in FIG. 1. That arrow also shows the direction in which airway adapter 22 is displaced to assemble it to transducer 24.

As is best shown in FIG. 4, apertures 54 and 56 are formed in the center section 42 of airway adapter 22. With transducer 24 assembled to the airway adapter, these apertures are aligned along an optical path identified by reference character 58. That optical path extends from the infrared radiation emitter unit 28 in transducer 24 transversely across airway adapter 22 and the gas(es) flowing therethrough to the infrared radiation detector unit 30 of transducer 24.

To: (a) keep the gases flowing through airway adapter 22 from escaping through apertures 54 and 56 without attenuating the infrared radiation traversing optical path 58, and (b) keep foreign material from the interior of the airway adapter, the apertures are sealed by sapphire windows 60 and 62 (see FIGS. 1 and 4). And, perhaps even more importantly, these windows define an optical path of precise length for the radiation traversing the optical path. This is important because the radiation is attentuated to an extent proportional to the number of molecules of the designated gas between those windows and in that volume circumscribed by the windows. Consequently, even small variations can significantly affect the accuracy of an ultimately produced, concentration indicative signal.

Sapphire windows are employed because other materials such as glass or plastic would absorb the infrared radiation to an extent that would significantly degrade the quality of the signals generated in detector unit 30.

Referring now primarily to FIGS. 1, 2B, and 4, that casing 26 of transducer 24 in which the source unit 28 and detector unit 30 are housed includes a generally U-shaped component 64 having first and second end sections 66 and 68 with a rectangularly configured gap 70 therebetween. With the transducer assembled to airway adapter 22 (see FIG. 4), the two sections 66 and 68 of transducer casing 26 embrace those two inner side walls 72 and 74 of the airway adapter central section 42 in which energy transmitting windows 60 and 62 are installed.

Optically transparent windows 76 (FIGS. 1 and 4A) and 78 (FIG. 4) are installed along optical path 58 in apertures 80 and 82 provided in the inner end walls 84 and 86 of transducer housing 26. These windows allow the electromagnetic energy beam 88 emitted by unit 28 and depicted in FIG. 4 to pass from the emitter unit 28 in the left-hand end section 66 of transducer housing 26 to airway adapter 22 and from the airway adapter to the detector unit 30 in the right-hand section 68 of the transducer housing. At the same time, windows 76 and 78 keep foreign material from penetrating to the interior of the transducer casing.

The power supply 32, amplifier PCB 38, electrostatic shield 40 are also mounted in the right-hand section 68 of casing 22.

Like airway adapter 22, the unit 28 employed to emit electromagnetic radiation, form that energy into a beam, and propagate the beam along optical path 58 is not, by itself, part of the present invention. Consequently, as is the case with the airway adapter, the radiant energy emitter or source unit 28 will be described herein only to the extent that it relates to the present invention and/or is necessary to an understanding of that invention.

Turning then to FIGS. 2A and 4, the emitter or source unit 28 includes a support 92 for an infrared radiation emitter 94. The latter may be of the unique thick film construction disclosed in U.S. Pat. Nos. 4,859,858 and 4,859,859.

Also mounted on support 92 is a parabolic mirror 96. This component collimates the energy emitted from emitter 94 and propagates the resulting beam along optical path 58 through the sapphire window 76 in the emitter housing casing section 66.

Generation of a detector output signal of a high enough signal-to-noise ratio to be useful requires that the beam of attenuated infrared radiation falling on the detector be modulated. It was pointed out in U.S. Pat. Nos. 4,859,859 and 4,859,858 this can be done by applying electrical pulses to an electrically resistive, emissive component of the electromagnetic energy source. One system for supplying such pulses is shown in FIG. 7 and identified by reference character 100.

That system includes an H bridge driver 102 with the emitter 94 of infrared source unit 28 connected across its outputs and timing circuits, collectively identified by reference character 104. Circuits 104 supply timing signals to driver 102. The timing signals are derived from a crystal oscillator (not shown) and then counted down to provide the desired pulse rate and duty cycle. A current implementation uses a 7 MHz oscillator to provide a 85.45 Hz pulse rate at a 7.1 percent duty cycle.

The driver contains logic circuits and power MOSFETs arranged in the so-called "H" configuration. This provides the capability to turn on opposite legs of the "H" so that the emitter 94 is easily driven in opposite directions. The magnitude of the voltage applied to the source is controlled by changing the Vp voltages.

Figure 7:
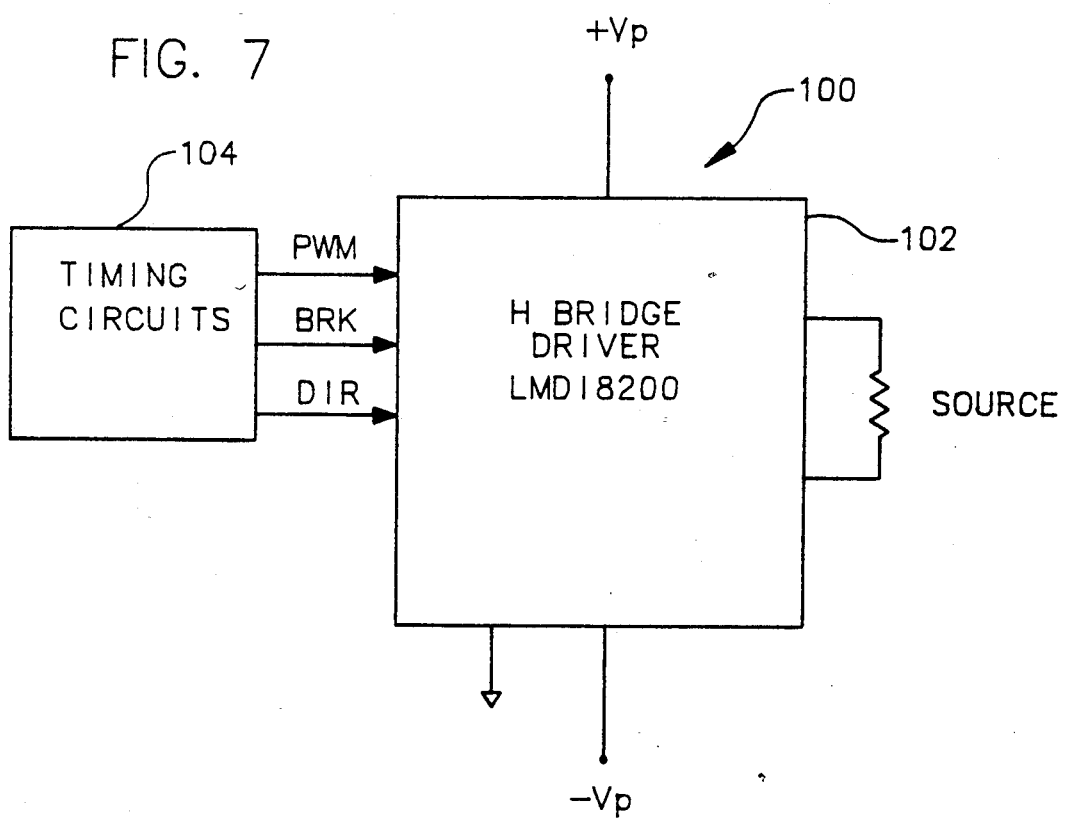
FIG. 7 is a block diagram of a system incorporated in the transducer to provide pulsed operation of an infrared source also incorporated in the transducer and used to emit infrared radiation that can be attenuated by the gas of interest to an extent proportional to the concentration of that gas.

Bipolar pulsing, whether provided by the circuitry shown in FIG. 7 or in some other manner, is preferred. Pulsing of this character eliminates the hysteresis and other adverse effects of continually pulsing the emitter with energy of the same polarity.

The details of the bipolar power supply 100 illustrated in FIG. 7 are, once again, not part of the present invention. Consequently, they will not be alluded to further herein.

The just-discussed components of electromagnetic energy source 28 are mounted on a printed circuit board 106. The resulting assembly is installed in the left-hand end section 66 of transducer casing 26. The assembly is retained in place by screws 108. These extend through apertures 110 in the printed circuit board and are threaded into complementary apertures (not shown) in transducer casing 26.

Referring now to FIGS. 2B through 6, it will be remembered that the detector side of transducer 24 includes a detector unit 30, a power supply 32 for supplying biasing voltage to the detector unit, and detector amplifiers 34 and 36.

As is perhaps best shown in FIG. 4, detector unit 30 includes a boxlike housing 112 mounted on a printed circuit board 113. A monolithic, heat conductive, isothermal support 114 is installed in housing 112. This component is preferably extruded from aluminum because of the high heat conductivity which that element possesses.

Isothermal support 114 has a generally L-shaped configuration with two normally related, integral legs 116 and 118 separated by a transition section 120. The isothermal support is installed in detector unit housing 112 with locating and retaining lugs 122, 124, and 126 in housing component 128 engaged in cooperating recesses 132, 134, and 136. These are located in the leg 116, transition section 120, and leg 118 of isothermal support 112.

Figure 8:
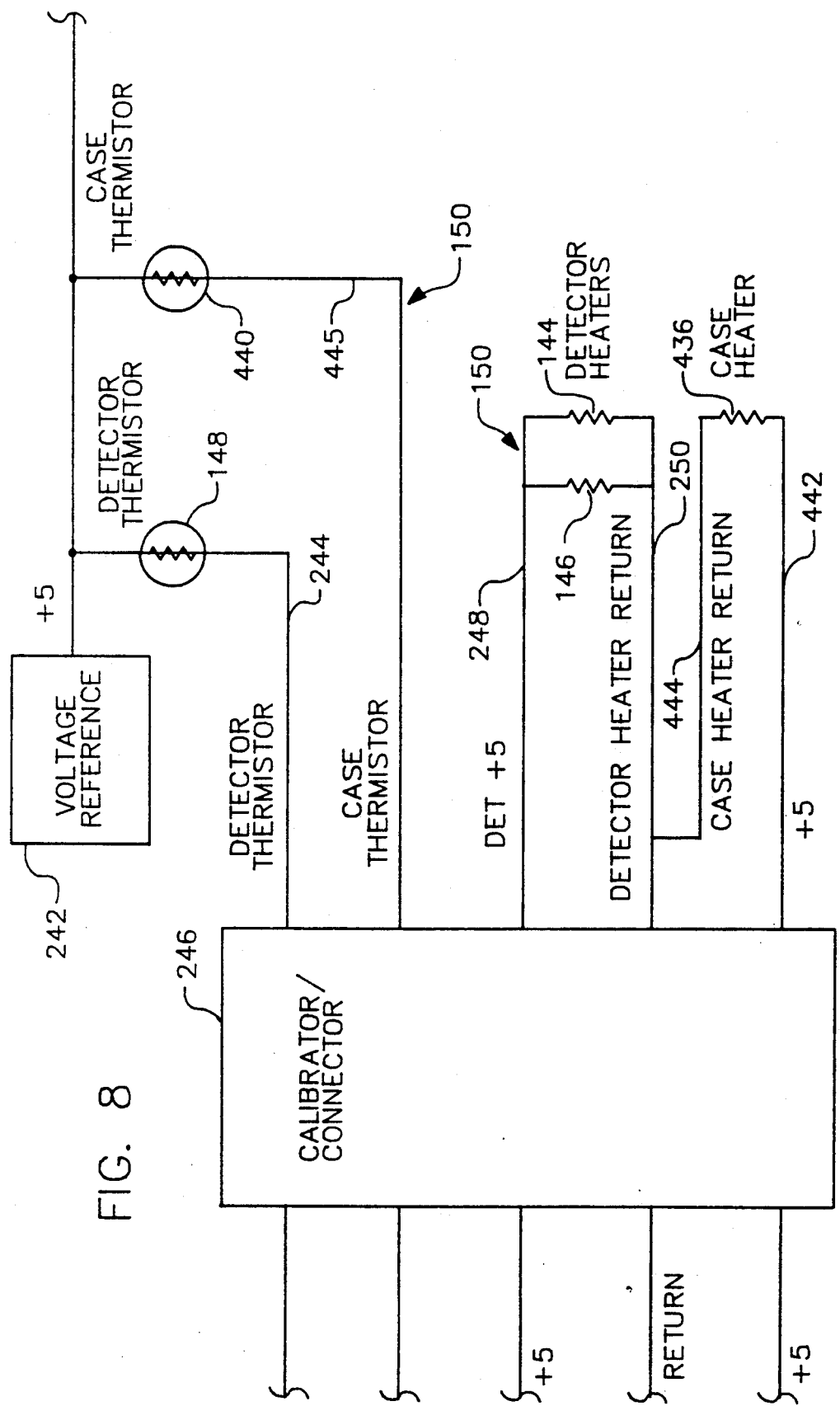
FIG. 8 is a schematic of systems employed in the detector unit to keep the coaxial detectors at the same, selected, unvarying temperature and to keep the casing of the airway adapter at an elevated temperature.

Supported from and mounted in support 112 are: (a) data and reference detectors 138 and 140, (b) a beam splitter 142, and (c) the detector heaters 144 and 146 and thermistor-type current flow-limiting device 148 of a detector heater system 150 (FIG. 8). That system is employed to keep the two detectors at exactly the same, selected temperature, typically with a tolerance of not more than 0.01° C.

Detectors 138 and 140 are preferably fabricated with lead selenide detector elements because of the sensitivity which that material possesses to electromagnetic energy having wavelengths which are apt to be of interest.

The two detectors 138 and 140 will typically be identical. Data detector 138 (see FIG. 5A) is representative. It has a single crystal, quartz substrate 152 with an exposed surface 154 on which titanium, gold electrodes 156 and 158 and are plated. A thin, lead selenide detector element 160 of the same rectangular shape as, but smaller than, substrate 152 is also placed on the surface 154 of the substrate (see FIG. 5A). The ends of this element lap onto, and are in electrical contact with, electrodes 156 and 158.

The electrodes of each detector are connected to +10 V and −10 V outputs from power supply 32 to impress a necessary biasing voltage across the detector element 160 of the detector.

Figure 5:
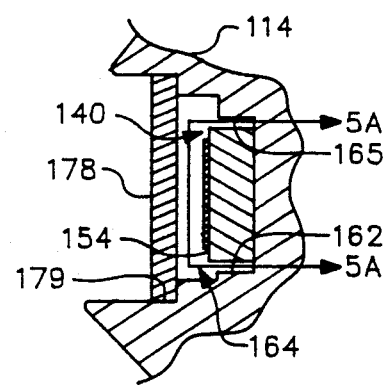
FIG. 5 is a fragment of FIG. 4, drawn to a larger scale to better show a detector mounting system which electrically isolates data and reference detectors of the detector unit from their support.
Figure 5A:
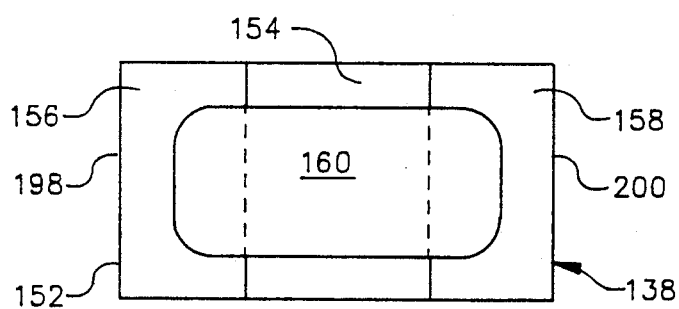
FIG. 5A is a plan view of the reference detector, looking in the direction of arrows 5A—5A in FIG. 5.

Each of the two detectors 138 and 140 is mounted in the innermost step 162 of a stepped recess 164 opening onto the front side of heat conductive support 114. As is best shown in FIG. 5, step 162 is so dimensioned with respect to the detector 138 or 140 mounted in that recess as to leave a gap 165 around the periphery of the detector and between the detector and isothermal support 114. This electrically isolates the conductive electrodes 156 and 158 on the detector substrate 152 from the also conductive, isothermal support 114.

Referring again to FIG. 4, beam splitter 142 has a generally parallelepipedal configuration. This component is fabricated from a material such as silicon or sapphire which is essentially transparent to electromagnetic energy with wavelengths of interest. The exposed front surface 168 of the beam splitter (FIG. 4B) is completely covered with a coating (not shown) capable of reflecting that electromagnetic energy impinging on the beam splitter which has a wavelength longer than a selected value. Preferred is a proprietary coating supplied by Optical Coating Laboratories, Inc., Santa Rosa, Calif. In the illustrated exemplary embodiment of the invention, the coating 170 will reflect to data detector 138 as indicated by arrow 172 in FIG. 4 energy having a wavelength longer than about 4 microns. The energy of shorter wavelengths is, instead, transmitted through coating 170 and the beam splitter to reference detector 140 as is suggested by arrow 174 in the same figure.

Bandpass filters 176 and 178 also supplied by Optical Coating Laboratories, Inc. limit the electromagnetic energy respectively reflected from and transmitted by beam splitter 142 and impinging upon detectors 138 and 140 to energy in selected bandwidths. In the exemplary embodiment and use of the invention under discussion and depicted in the drawing, the reference detector filter 178 in detector unit 30 is centered on a wavelength of 3.681 $\mu$m and has a half power bandwidth of 0.190 $\mu$m. That filter transmits maximum energy near the band absorbed by data detector 138; but there are no interfering gases that would absorb in the transmitted bandwidth. Nitrous oxide and water, the gases most apt to interfere, absorb on opposite sides of that bandwidth so the selected region is almost certain to be one where there is no absorption. This absorption of maximum energy in an adjacent bandwidth is selected so that the output from reference detector 140 will be at least as large as the output from data detector 138. This contributes markedly to the accuracy of the gas concentration indicative signal subsequently obtained by ratioing the data and reference signals.

The data detector bandpass filter 176 is centered on a wavelength of 4.260 $\mu$m and has a bandwidth of 0.10 $\mu$m. This is two times narrower than the band passed by filter 178. The carbon dioxide absorption curve is fairly narrow and strong, and bandpass filter 176 centers the transmission band within that absorption curve. Therefore, if there is a change in carbon dioxide level in the gas(es) being analyzed, the maximum modulation for a given change in carbon dioxide level is obtained. If the electromagnetic energy otherwise reached the data detector through the bandpass filter whether or not carbon dioxide was present in the gases being analyzed, the modulation of the carbon dioxide related output of data detector 138 would decrease, and accuracy would suffer.

Referring now to both FIG. 4 and FIG. 5, each of the bandpass filters 176 and 178 is mounted in the outer step 179 of that recess 164 in monolithic, isothermal support 114 in which the associated detector 138 or 140 is mounted (FIG. 5).

As shown in FIG. 4, the upper edge 180 of beam splitter 142 is fitted into a recess 182 in monolithic, isothermal support transition section 120 exactly midway between the bandpass filter 176 in front of data detector 138 and the bandpass filter 178 in front of reference detector 140. The opposite, lower part 184 of the beam splitter is fixed, as by epoxy adhesive 186, to an inclined, integral lip 188 which extends inwardly from detector unit casing component 190. This positively, and accurately, locates beam splitter 142 relative to data detector 138 and reference detector 140.

Figure 13:
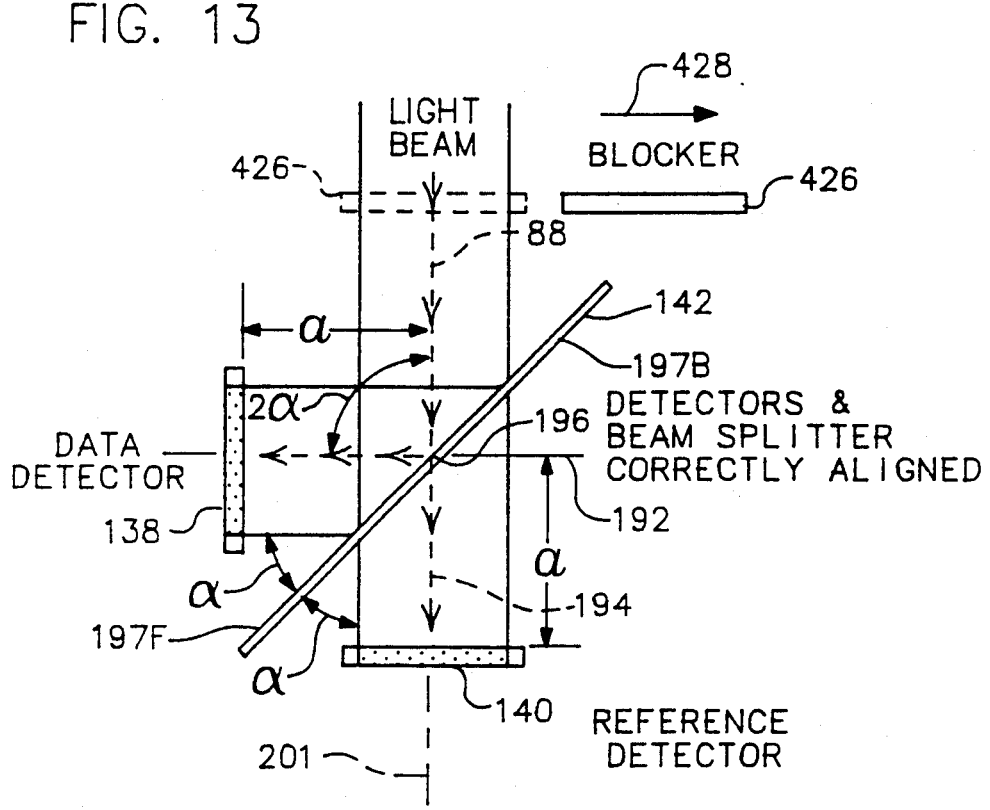
FIG. 13 is a schematic view of the detector unit optical system with the beam splitter employed to direct energy of different wavelengths to the data detector and the reference detector properly aligned relative to the detectors.

The exposed surfaces 154 of the data and reference detectors 138 and 140 are identically configured and dimensioned. The two detectors are oriented: (a) at the same angle $\alpha$ relative to, and at equal distances from, beam splitter 142 (FIG. 13); (b) with the longitudinal planes of symmetry 192 and 194 of the data detector 138 and reference detector 140 intersecting in the plane of symmetry 196 of beam splitter 142 between its front and back surfaces 197F and 197B; (c) with the distances from the opposite edges 198 and 200 of the data detector (and the reference detector) the same (see dimensions a in FIG. 13) so that neither data detector 138 nor reference detector 140 are skewed with respect to beam splitter 142; and (d) with the respective edges 198 and 200 of the two detectors 138 and 140 precisely aligned (FIG. 4A). In the particular arrangement shown in FIGS. 4 and 13, the longitudinal axis of symmetry 192 of data detector 138 is at an angle of 2 $\alpha$ relative to the longitudinal axis of symmetry 201 of beam 88. The longitudinal axis of symmetry 194 of reference detector 140 coincides with beam axis 201.

As will be apparent from the foregoing discussion and the several illustrations of the optical components in detector unit 30, all of that energy over the entire and same span of the beam 88 reaching detector unit 30 with a wavelength longer than the selected cutoff is reflected to data detector 138. Similarly, over the entire span of the beam, that energy with a shorter wavelength is transmitted through beam splitter 142 to reference detector 140. Because of this, the relationship of detectors 138 and 140 discussed above, and the identical dimensioning and configuration of the energy intercepting surfaces 154 of those detectors, both detectors "see" the same image of the beam 88 of electromagnetic energy. As indicated above, this contributes markedly to the accuracy afforded by detector unit 30.

In other words, and optically, with the data and reference detectors 138 and 140 accurately positioned relative to each other and beam splitter 142 in the novel manner just described, these components function as if the two detectors were precisely stacked one on top of the other. Therefore, electromagnetic energy from the entire compass of the beam reaches both detectors in spatially identical fashion.

Furthermore, the two signals to the data and reference detectors are identical in time inasmuch as the detector-to-beam splitter distances are equal and the time required for the reflected and transmitted components of beam 88 to travel from beam splitter 142 to each of the two detectors 138 and 140 is, therefore, the same. Consequently, the novel, optical arrangement disclosed herein has the advantage of a coaxial detector arrangement in that the effect of spatial variations are eliminated. However, the disclosed detector arrangement has the advantage that time variations are eliminated. This is not the case in a coaxial detector because one detector is located in front of the other. Incoming electromagnetic energy therefore reaches that detector before it reaches the second detector.

By making the two detectors 138 and 140 spatially coincident from the optical viewpoint, and coincident in time, the adverse effects on accuracy attributable to foreign material collecting on any of the optical windows 60, 62, 76, or 78 and a subsequently described window of detector unit 30 are also eliminated by the subsequent ratioing of the data and reference detector output signals.

The electromagnetic energy in beam 88 reaches beam splitter 142 through an aperture 202 in the front side 204 of detector unit casing component 190. A typically sapphire window 206 spans aperture 202 and keeps foreign material from penetrating to the interior 208 of detector unit housing 112 before the detector unit is installed in transducer housing 26 and if that housing is subsequently unsealed.

To exclude extraneous energy, and thereby ensure that only the energy in beam 88 reaches beam splitter 142, light traps 210 and 212 are provided (see FIGS. 4 and 6). The first of these is a triangularly sectioned, inwardly extending, projection of monolithic, isothermal support 114. The second, cooperating light trap 212 is aligned with, fixed in any convenient fashion to, and extends inwardly from the casing-associated ledge or lip 188 from which the lower side 184 of beam splitter 142 is supported.

The operation of transducer 24 as thus far described is believed to be apparent from the drawing and the foregoing, detailed description of the transducer. Briefly, however, electromagnetic energy in the infrared portion of the spectrum is generated by heating the source or emitter 94 of emitter unit 28, preferably by applying bipolar pulses of electrical energy across the emitter unit as discussed above. The energy thus emitted is propagated toward the concave, emitter unit mirror 96 as shown by arrow 214 in FIG. 4. Mirror 96 collates and focuses this energy and propagates it in the form of beam 88 along optical path 58 across the gas(es) flowing through airway adapter 22.

Energy in a species specific band is absorbed by the gas of interest flowing through the airway adapter (typically carbon dioxide) to an extent proportional to the concentration of that gas. Thereafter, the attenuated beam passes through the aperture 202 in the front wall 204 of the detector unit casing component 190, intercepted by beam splitter 142, and either reflected toward data detector 138 or transmitted to reference detector 140. The bandpass filters 176 and 178 in front of those detectors limit the energy reaching them to specified (and different) bands. Each of the detectors 138 and 140 thereupon outputs an electrical signal proportional in magnitude to the intensity of the energy striking that detector. These signals are amplified by data detector amplifier 34 and reference detector amplifier 36 and then typically ratioed to generate a third signal accurately reflecting the concentration of the gas being monitored. The signal processor used for this purpose is independent of airway adapter 22 and transducer 24, not part of the present invention, and will accordingly not be disclosed herein.

The preferred, lead selenide detectors 138 and 140 are extremely temperature sensitive. It is therefore critical that these two detectors be maintained at the same temperature, preferably with the above-mentioned tolerance of not more than 0.01° C. Also, it was pointed out above that this desired degree of control is readily available from the detector heating system 150 made up of data detector heater 144, reference detector heater 146, and thermistor-type, temperature-limiting control 148.

Heaters 144 and 146 in that detector unit 30 illustrated in FIGS. 1–6 are precision, 25 ohm resistors with a tolerance of ±0.5 percent. Thermistor 148 is conventional and will accordingly not be described in detail herein.

Referring now specifically to FIG. 4, the circularly sectioned resistance heaters 144 and 146 are installed in complementary, circularly sectioned recesses 216 and 218 extending from side-to-side in the legs 116 and 118 of monolithic, isothermal support 114, producing efficient, conductive heat transfer between the heaters and the support. Thermistor 148 is installed in a similar, transversely extending, complementary aperture 220 in isothermal support transition section 120. The spatial relationship between heater 144 and data detector 138 and between heater 146 and reference detector 140 are identical, and the spatial relationship between thermistor 148 and each of the heaters 144 and 146 is also identical. Furthermore, the two heaters 144 and 146 are so located with respect to the associated detectors 138 and 140 that the thermal energy emitted from the heaters travels first across the detectors and then across the current flow-limiting thermistor 148 to heat dumps provided by gaps 222 and 223. These are respectively located between: (a) the leg 116 of isothermal support 114 and the top wall 224 of detector unit housing component 128, and (b) the rear wall 226 of the housing component and the leg 118 of the isothermal support. The heat flow paths are identified by arrows 228 and 230 in FIG. 4. As a consequence of the foregoing and the high thermal conductivity of isothermal support 114, the data and reference detectors 138 and 140 can readily be maintained at the same temperature.

Plus 5 V power is made available to the two detector heaters 144 and 146 under the control of thermistor 148 through leads 232 in an external power cable 234 and leads 236 on detector unit printed circuit board 113. Power cable 234 extends through an opening (not shown) in transducer casing 26. Its transducer-associated end is attached to casing 26 by a strain relief fitting 240.

A wiring diagram for detector heating system 150 is shown in FIG. 8. Turning then to it, the data detector heater 144 and reference detector heater 146 are supplied with +5 V power from a voltage reference or regulator 242 incorporated in power supply 32. This voltage is modulated by the thermistor 148 of heating system 150 to control the output from the detector heaters and maintain isothermal support 114, — and therefore data and reference detectors 138 and 140 — at a constant, uniform temperature.

Detector thermistor 148 is located between and connected to two sections of a lead 244 in external power cable 234. That lead extends from voltage regulator 242 to a calibrator/connector 246 which may be located at some distance from transducer 24.

Unit 246 is, like others illustrated in the drawings, not by itself a part of the present invention. It will, for that reason, not be described in detail herein.

A further lead 248 in external power cable 234 supplies the modulated, +5 V power to heaters 144 and 146 from calibrator/connector 246; and a return lead 250 completes the circuit to that unit.

Various other ones of the conductors in cable 234 are connected physically to the printed circuit board 106 of emitter unit 28 and the printed circuit board 38 of detector unit 30. Electrically, these leads are connected to: (a) the power supply 100 of the emitter unit, (b) the power supply 32 in the detector unit, and (c) the output side of the amplifiers 34 and 36 employed to increase the levels of the signals outputted from detectors 138 and 140 and make those signals less susceptible to interference by 60 Hz or other electrical energy radiated into the surrounding environs.

As discussed above, it is one function of power supply 32 (see FIGS. 2, 9, and 12) to make a precisely controlled voltage available to data detector heater 144 and to reference detector heater 146 so that those two detectors can be maintained at exactly the design operating temperature. Typically, +15 V and −15 V signals are inputted to power supply 32 through external cable 234.

A power line bypass capacitor C252 is connected between the +15 V input to power supply 32 and ground, and a matching capacitor C258 is connected between the −15 V input and ground. Those capacitors filter out high frequency noise present in the incoming signal, making it possible to create clean, noise-free signals for biasing the data detector 138 and reference detector 140. Capacitors C252 and C258 also suppress oscillations that may appear in the signal inputted to power supply 32.

Figure 12:
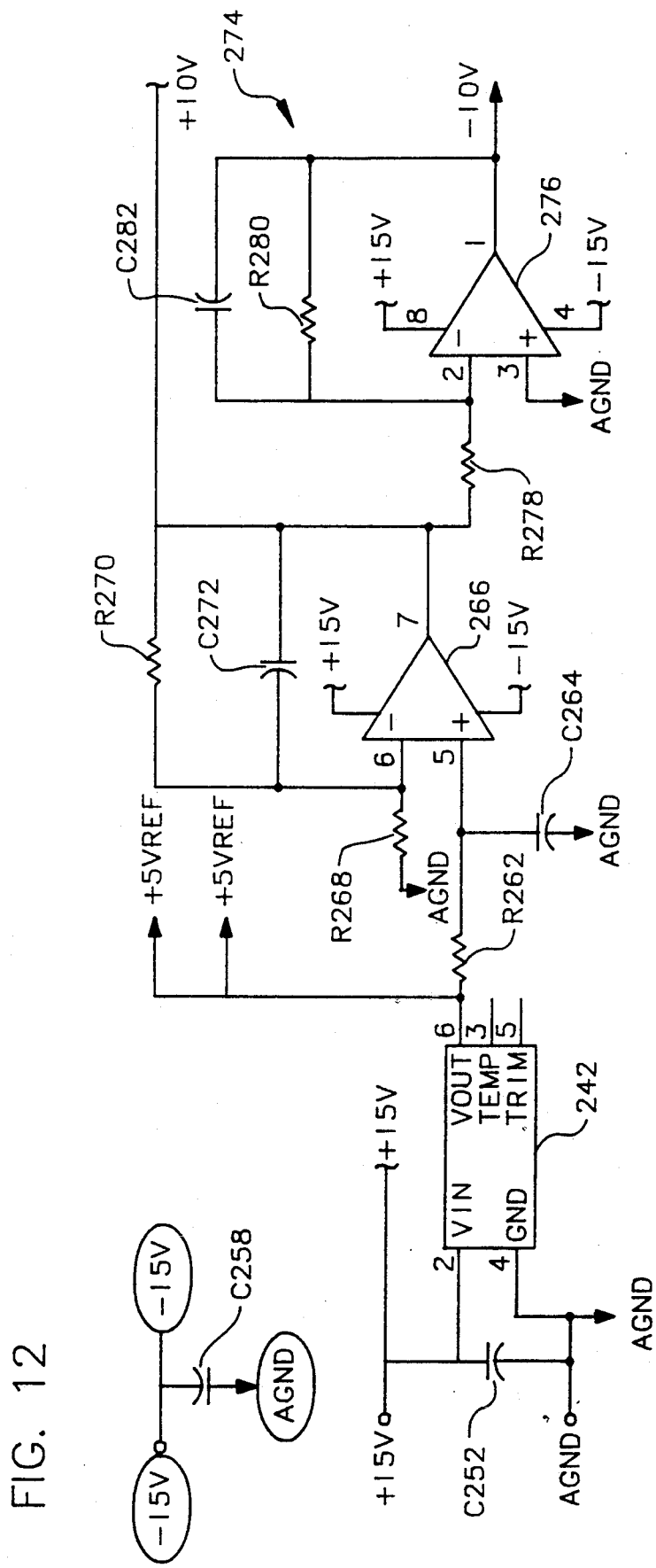
FIG. 12 is an electrical schematic of a power supply incorporated in the system of FIG. 9 to provide the requisite operating voltages.

Continuing with FIG. 12, the +15 V signal is made available to data and reference detector amplifiers 34 and 36. The +15 V signal is also inputted to pin 2 of the above-mentioned, solid state voltage regulator 242, which has a second terminal 4 connected to ground.

Voltage regulator 242 outputs a +5 V reference or biasing voltage for data and reference detector amplifiers 34 and 36 and the same voltage for data and reference detector heaters 144 and 146. The +5 V signal is outputted from voltage regulator 242 at terminal 6.

Voltage regulator 242 has two additional terminals 3 and 5. Terminal 3 is used in providing temperature compensation. Terminal 5 is intended to be connected to a trimming resistance to optimize the accuracy with which the voltage regulator outputs the 5 V reference voltage.

Figure 9:
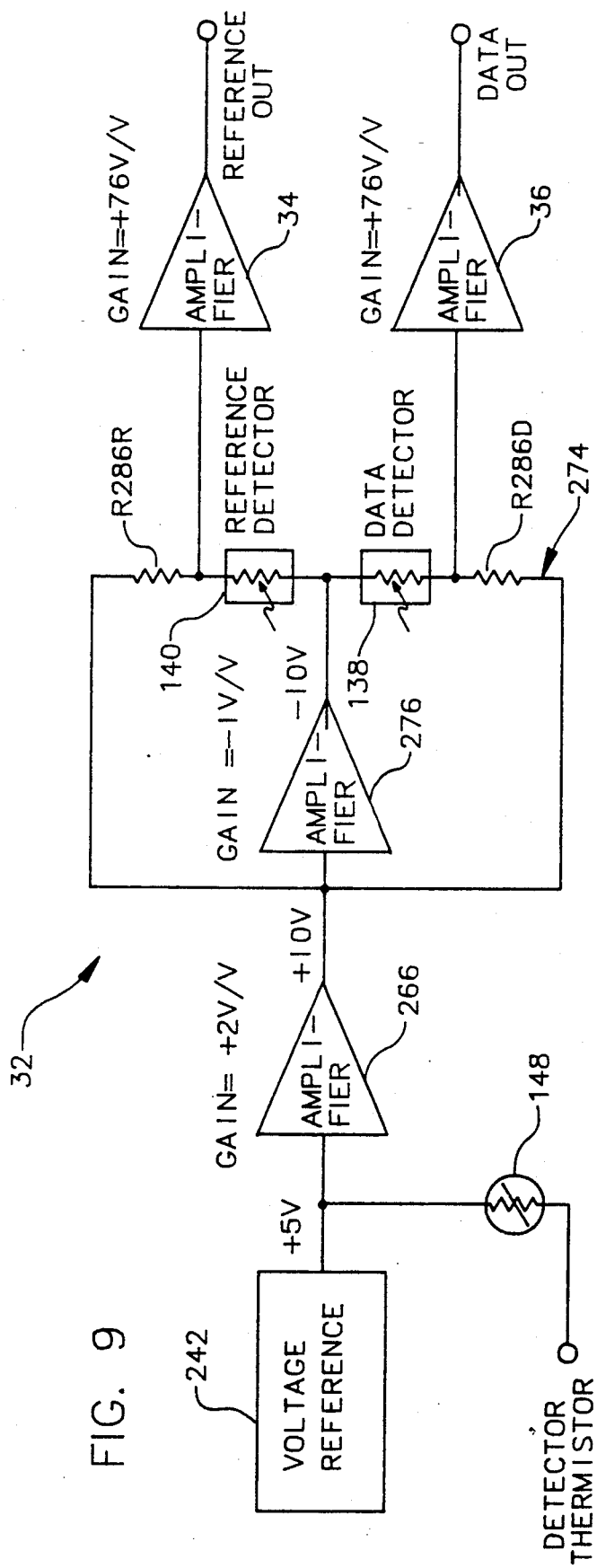
FIG. 9 is a block diagram of a system employed in the transducer to supply power at appropriate voltages to the electrical components of the transducer and to amplify the signals outputted by the reference and data detectors.

Referring still to FIGS. 9 and 12, the +5 V reference voltage is also applied to a noise filter consisting of resistor R262 and bypass capacitor C264. This eliminates excessive noise from the signals outputted from data and reference detectors 138 and 140. The filtered signal is transmitted to the non-inverting terminal 5 of an operational amplifier (op amp) 266. The inverting terminal 6 of the op amp is connected to ground through impedance matching resistor R268.

Connected in parallel across op amp 266 are a feedback resistor R270 and a capacitor C272. Capacitor 272 provides low pass filtering and also assists in stabilizing the operation of op amp 266. Feedback resistor R270 has twice the resistance of biasing resistor R262 and therefore provides a positive gain of two, making a filtered +10 V signal available at the output terminal 7 of op amp 266.

The +10 V signal is also routed to an inverter 274 consisting of an op amp 276, resistors R278 and R280, and capacitor C282.

The latter components function in the same manner as their counterparts R262, R270, and C272 in the amplifier circuit based on op amp 266. In the case of inverter 274, however: (a) the incoming signal is supplied to the inverting terminal 2 of op amp 276; (b) the non-inverting terminal 3 is connected to ground; (c) resistors R278 and R280 are equal in resistance; and (d) a filtered −10 V signal accordingly appears at the output terminal 1 of op amp 276.

The +10 V and −10 V signals are applied to opposite sides of data detector 138 and to the opposite sides of reference detector 140 (see FIG. 9). This biases detectors 138 and 140 to the maximum extent. That is important because the sensitivity of those detectors to energy in the electromagnetic portion of the electromagnetic spectrum is bias dependent. Therefore, as the bias is increased; the magnitude of the signal that can be outputted for a given quantum of impinging energy is increased. However, the signals outputted from the detectors are small; and signal-to-noise ratio is accordingly a significant consideration. Twenty volts adequately biases the detectors and can be supplied without the high voltage transformer that would be needed if a higher bias voltage were selected.

Figure 10:
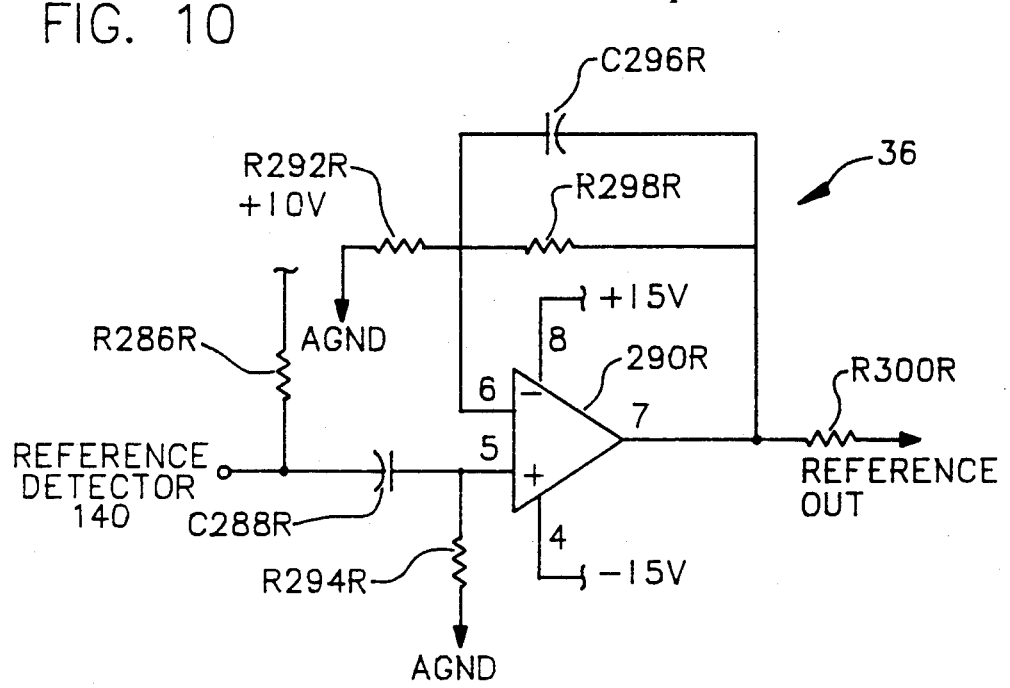
FIG. 10 is a an electrical schematic of a reference detector amplifier employed in the system shown in FIG. 9.
Figure 11:
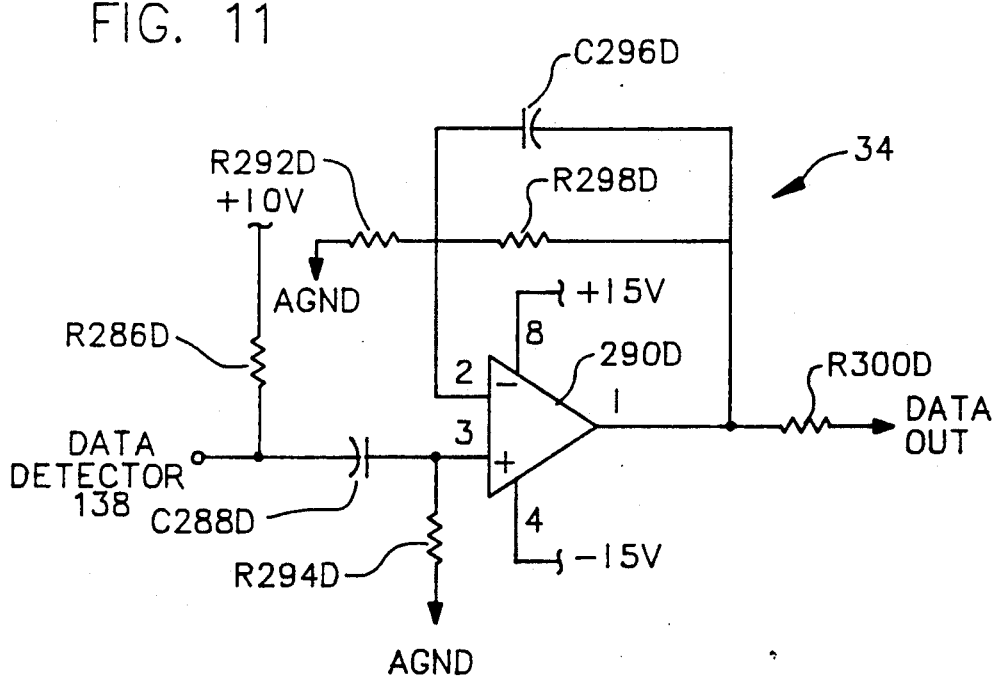
FIG. 11 is an electrical schematic of a data detector amplifier employed in the system shown in FIG. 9.

Referring still to FIG. 9, it will be remembered that transducer 24 also includes a data detector amplifier 34 and a reference detector amplifier 36 (shown in more detail in FIGS. 10 and 11). In the exemplary embodiment of the invention under discussion, both of these amplifiers have a gain of 76 V/V. The two detector output amplifiers 34 and 36 are essentially identical. Consequently, the corresponding components of both amplifiers will be identified by the same reference characters followed by the letter "D" for data detector output amplifier 34 and by the letter "R" for reference detector output amplifier 36; and only data detector output amplifier 34 will be described in detail.

Referring then specifically to FIG. 11, amplifier 34 includes a bias resistor R286D in series with data detector 138 and the filtered +10 V output from power supply 32. The biasing resistor limits the flow of current through detector 138 to a level which serves to optimize the signal-to-noise ratio of the signal outputted from detector 138 as electromagnetic energy falls on that detector. That is, if the magnitude of the current through the detector is either below a lower limit or above an upper limit, the signal-to-noise ratio of the outputted signal will increase materially. Bias resistor R286D ensures that the current flow will lie between these lower and upper limits.

Typically, biasing resistor R286 will have a resistance on the order of 750 Kohm. The dark resistance of the lead selenide detectors employed in the exemplary, illustrated embodiment of the invention typically varies from 400 Kohm to 2 Mohm. A 750 Kohm resistor is capable of satisfactorily controlling the current flow of detectors with a dark resistance in that range. Optimum accuracy of the signal outputted from the detectors can of course be obtained by matching the resistance of resistor R286D to the resistance of each particular detector if the considerable cost of doing so warrants.

The biased data detector output signal is AC coupled through a capacitor C288D to the non-inverting terminal 3 of an op amp 290D. A resistor R292D connected to ground between capacitor C288D and op amp 290 provides high pass filtering and keeps the incoming signal at ground, eliminating input offset errors.

The inverting terminal 2 of op amp 290 is connected to ground through a resistor R294D. That resistor provides impedance matching between the input and output sides of op amp 290D.

Other major components of amplifier 34 are a capacitor C296D and resistors R298D and R300D. Capacitor C296D provides signal frequency, low pass filtering and stabilizes op amp 290. The combination of that capacitor and resistor R300D removes high frequency noise from the amplified signal. Resistor R300D also provides the requisite gain in the feedback circuit of amplifier 34 and a low impedance on the output side of op amp 290D. This tends to keep EMI-type energy emitted from extraneous sources such as the various pieces of equipment in an operating room from degrading the signal outputted by op amp 290 and to provide at least some protection against signal line shorts.

Plus and minus 15 V signals are impressed on the input terminals 8 and 4 of the just-described operational amplifier 290D (and its counterpart 290R in reference detector amplifier 36) and, also, on the corresponding terminals of the operational amplifiers 266 and 276 in detector unit power supply 32. These signals ensure that the range of each amplifier (including inverter 274) is greater than the variation in magnitude of the amplified signal outputted from it and, consequently, that the rails are not hit during the operation of the amplifiers Additional, and comprehensive, electrostatic shielding is provided by the electrostatic shield 40 illustrated in FIG. 2B. The main component 302 of this shield is a box with a generally rectangular configuration. The forward end 304 of component 302 is closed; and it has two barndoor-type closures 306 and 308 at the opposite, rear end.

Electrostatic shield 40 is preferably fabricated from mild steel and nickel plated for ease of solderability. This provides satisfactory shielding at a cost much lower than can be obtained by utilizing alternatives such as a heretofore employed, sprayed nickel coating.

A platelike support and shielding component or floor 310 is mounted in the boxlike, main component 302 of shield 40 toward the bottom 312 of the latter. Spaced above that component and fixed to the side walls 314 and 316 of component 302 opposite each other and parallel to floor 310 are guides 318 and 320.

As is shown in FIG. 2B and also in FIGS. 4 and 6, and as discussed above, detector unit housing 112 with its internal components is physically attached to the printed circuit board 113 to complete the assembly of transducer 24. Integral prongs 322 on the rear wall 226 of detector unit housing component 128 extend through apertures 324 in the printed circuit board to accurately locate housing 112 on printed circuit board 113. Electrical connections between components housed in casing 128 and appropriate leads 236 on PCB 113 are made by pins 323 (FIG. 6).

The resulting detector unit 30 is installed in electrostatic shield 40 between floor 310 and the upper guides 318 and 320 by displacing the assembly as suggested by arrow 326 in FIG. 2B.

Once detector unit 30 has been installed in shield 40: (a) guides 318 and 320 keep the assembly from moving up and down in electrostatic shield 40, (b) the two side walls 314 and 316 of the shield keep the assembly from moving side to side, and (c) the wall (not shown) at the front end of the shield 40 keeps the assembly from moving forward in the shield. Assembly is completed by bending down the integral tabs 328 and 330 at the rear end of guides 318 and 320 and then soldering those tabs to the backplane of printed circuit board 113. These tabs extend through holes 331 in printed circuit board 115 and space detector unit casing 26 away from the sides and bottom of electrostatic shield 40. That electrically isolates the detector unit housing from the shield.

Next, the shielded detector unit is installed in the right-hand end 68 of transducer casing 24.

Specifically, in and extending longitudinally of transducer casing 26, are a series of guides 332 ... 358 for the shielded detector unit. Guides 332 ... 336 are on the inner surface of the right-hand wall 360 of housing end section 68, guides 338...344 on the inner surface of the bottom wall 362 of that section, guides 346 ... 350 on the inner surface of left-hand side wall 364, and guides 352 ... 358 on the inner surface of top wall 366.

The shielded detector unit 30 is installed in the right-hand end 68 of transducer casing 26 through the open, rear end 368 of that section as indicated by arrow 370 in FIG. 2B. As the detector unit slides into housing 26, sawtooth edges 371 on opposite sides of slots 372 (only one is shown) and 373 extending from the front toward the rear of electrostatic shield 40 and formed in the side walls 314 and 316 and floor 310 of that component engage: (a) corresponding upper surfaces of guides 332, 334 and 348, 350, and (b) the side surfaces of a guide 375 on the bottom wall 362 of detector casing right-hand end section 68. This keeps the shielded assembly from inadvertently falling out of transducer casing 26 during the assembly process.

As the shielded detector unit continues in the direction indicated by arrow 370, stops 376 provided by the rear ends of the shorter guides 340, 342, 354, and 356 are engaged by tabs 377 at the four corners of detector unit printed circuit board 113. That positions the shielded detector unit 30 in the fore and aft direction in transducer casing 26. Next, the two barndoors 306 and 308 at the rear of electrostatic shield 40 are closed; i.e., swung toward each other as indicated by arrows 378 and 379. This completes the shielding of detector unit 30.

Then, a tab 380 extending rearwardly from the boxlike, main component 302 of electrostatic shield 40 is bent upwardly (see FIG. 3) and soldered to the back plane 382 of printed circuit board 113. That grounds the components of detector unit 30.

After: (a) the steps just discussed; (b) the installation of the power supply/amplifier unit consisting of power supply 32, data detector amplifier 34, reference detector amplifier 36, and the printed circuit board 38 on which those systems are mounted in the slots 383 between guides 332/334 and 348/350; and (c) the installation of infrared radiation emitter unit 28 in the left-hand end section 66 of transducer casing 266, closures or end members 384 and 386 are assembled to the front (L-H) and rear (R-H) ends 388 and 390 of transducer casing 26. This isolates the operating components of that device from the ambient surroundings (see FIGS. 2A and 2B).

O-rings 392 and 394 seal the gaps between covers 384 and 386 and the corresponding ends 388 and 390 of casing 26. These seals keep air as well as other foreign matter from penetrating to the interior 398 of transducer casing 26. This is important because carbon dioxide in that air would adversely affect the accuracy of the concentration related signal outputted by data detector 138 and the accuracy of the reference signal with which the data signal is combined.

The efficacy of the sealing arrangement depicted in FIG. 2 was confirmed by immersing a transducer as shown in that figure in water. No leaks were found to have been caused by this immersion.

End members 384 and 386 are fastened to transducer casing 26 by a headed fastener 396.

Fastener 396 extends from head 397 seriatim through a recessed aperture 400 in right-hand end cover 390; an opening 402 through the printed circuit board 113 of detector unit 30; a circular opening provided by mirror image-related, half moon slots 406 in electrostatic shield barndoors 306 and 308 (one shown in FIG. 2B); and an aperture 408 through infrared source unit printed circuit board 38. The opposite, shank end 409 of fastener 396 is threaded into an internally threaded aperture 410. That aperture is formed in an integral boss 412 extending inwardly from the left-hand casing cover 388.

Fastener 396 clamps the assembly of covers, O-rings, and transducer housing together with the head 397 of the fastener seated in a recess 416. That recess is coaxial with the aperture 400 through right-hand cover 386. Then, a plate 418 is fastened to the right-hand cover over fastener head 397 to complete the assembly process. This plate is seated in a recess 420 in the right-hand cover 386. It is retained in place by an epoxy adhesive on posts (not shown) which extend inwardly from plate 418. These posts fit into apertures 421 in right-hand end member 386.

As has been discussed more than once above, it is critical with respect to the accuracy of a device or system employing data and reference detectors and a beam splitter for the purposes described above that these components be accurately aligned so that the same "image" will be viewed by the data detector and the reference detector. It is, therefore, equally important that one be able to identify data detector, reference detector, and beam splitter misalignments. Detector unit 30 admirably lends itself to quality control determinations of this character. The novel procedure employed can be best be understood by reference to: (a) FIGS. 13, 15, and 17, which respectively depict a detector unit with correctly aligned optical components, a graph of data obtained by the procedure confirming that those components are correctly aligned, and a plot of the raw data; and from FIGS. 14, 16, and 18, which are counterparts for a unit with a misaligned beam splitter.

Alignment of the data and reference detectors 138 and 140 in both the back-to-front and side-to-side directions can be, and preferably is, verified in the inspection process and misalignments in both directions identified. The procedure in both cases is the same. Consequently, in the interest of brevity, only the steps involved in verifying front-to-back alignment and identifying misalignments in that direction will be described below.

Inspection is conducted by first positioning a knife-edge blocker 426 oriented at a right angle to electromagnetic energy beam 88 across that aperture 202 in the front side 204 of the detector casing component 128 through which radiant energy reaches beam splitter 142. This blocking position is shown in dotted lines in FIG. 15. In the dotted line position, blocker 426 keeps radiant energy from reaching beam splitter 142 and data and reference detectors 138 or 140. Then, one rectilinearly and incrementally withdraws blocker 426 from the beam 88 in the direction indicated by arrow 428 until it completely clears the path traversed by electromagnetic energy beam 88. The voltage of the amplified signal outputted from each of the detectors 138 and 140 is recorded and plotted at each increment of withdrawal, and a curve connected to the thus obtained data points can be plotted.

Figure 15:
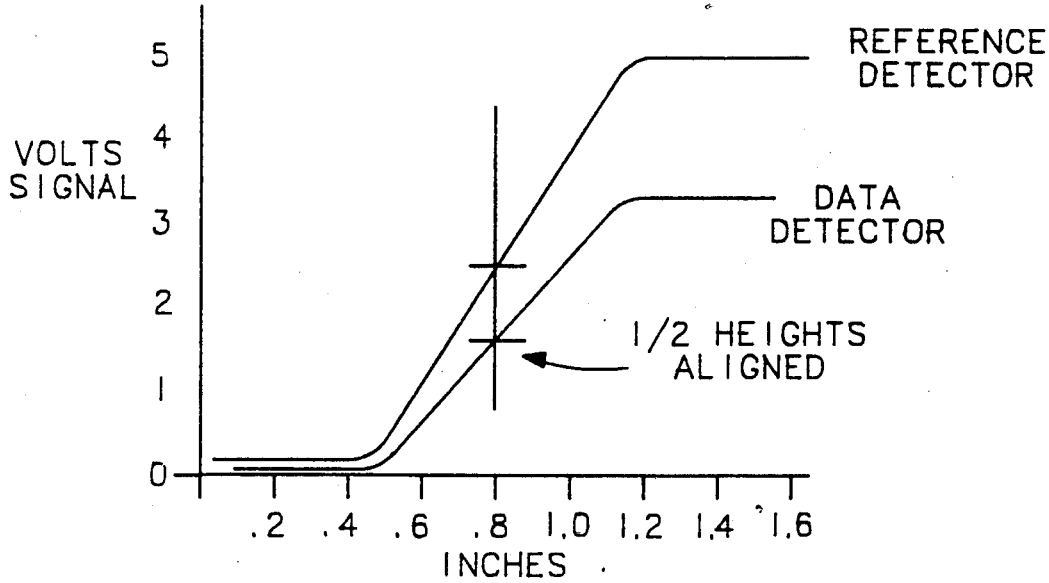
Figure 17:
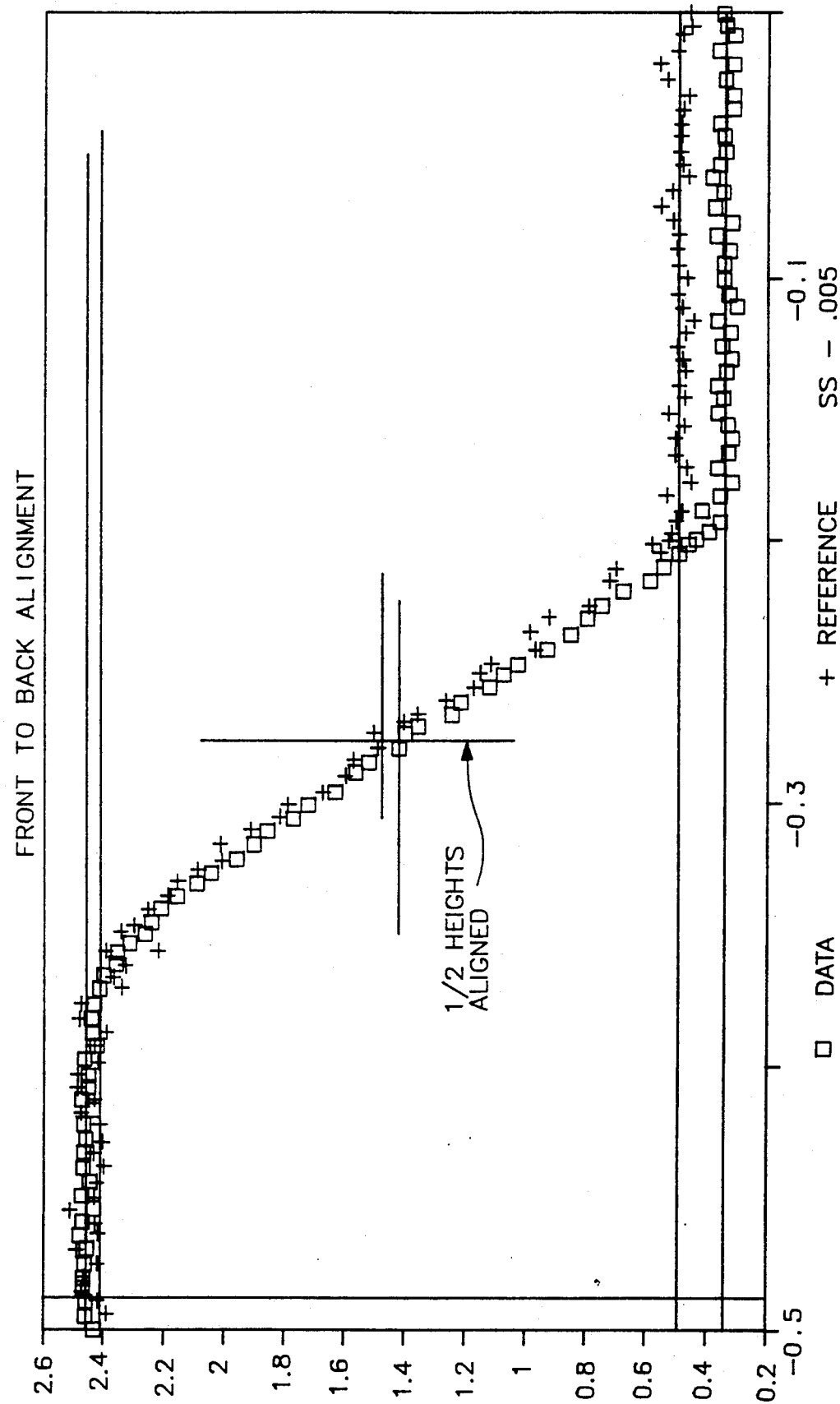
FIGS. 17 and 18 are plots of the raw data obtained from the knife edge scans.

If the optical components (the beam splitter and the data and reference detectors) are accurately aligned, both detectors will begin to output a signal at the same point of withdrawal of blocker 426 (see FIGS. 15 and 17). The maximum signal will also be outputted from the two detectors at the same point of withdrawal. The result is that the half heights — one half of the difference between the minimum and maximum voltages outputted by each detector — will be vertically aligned in a conventional, X-Y, output voltage vs. increment of withdrawal graph or data plot as shown in FIGS. 15 and 17.

Figure 14:
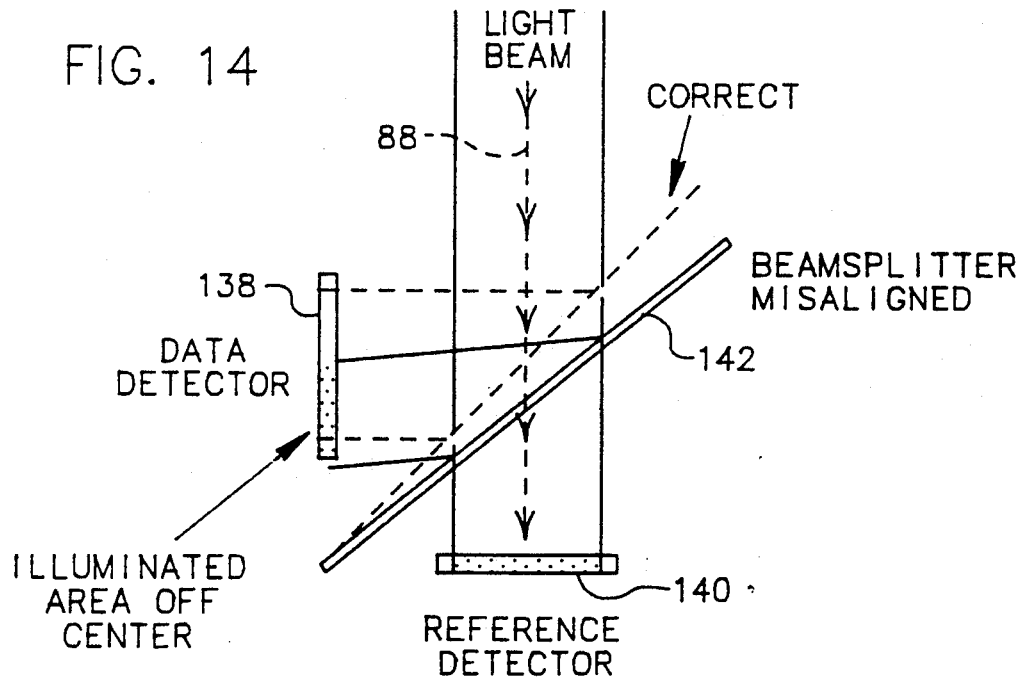
FIG. 14 is a similar schematic but with the beam splitter and detectors misaligned.
Figure 16:
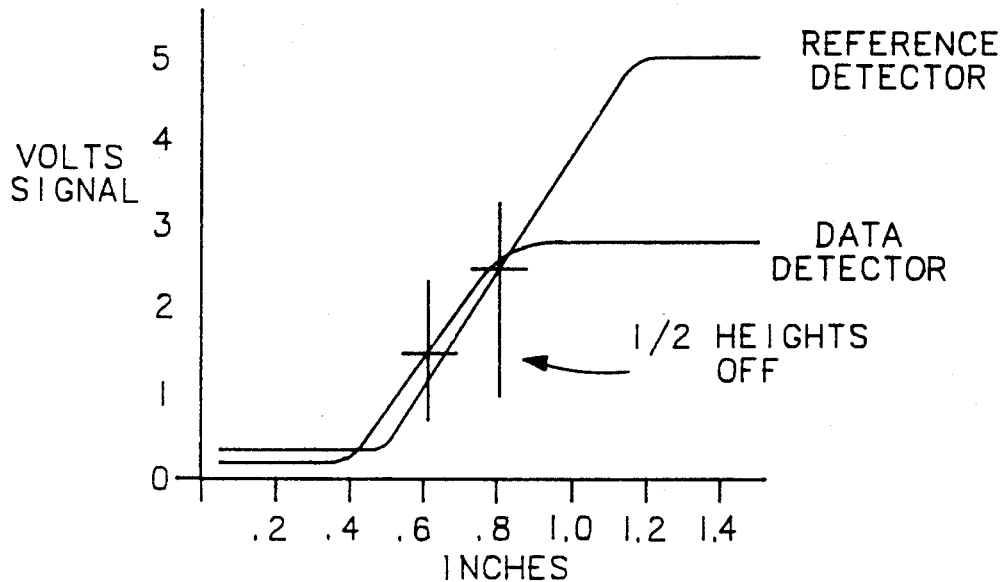
FIGS. 15 and 16 are graphs of data obtained from knife edge scans of detector units with misaligned and properly aligned optical components; a comparison of these two figures makes evident the degradation in performance attributable to optical misalignment.
Figure 18:
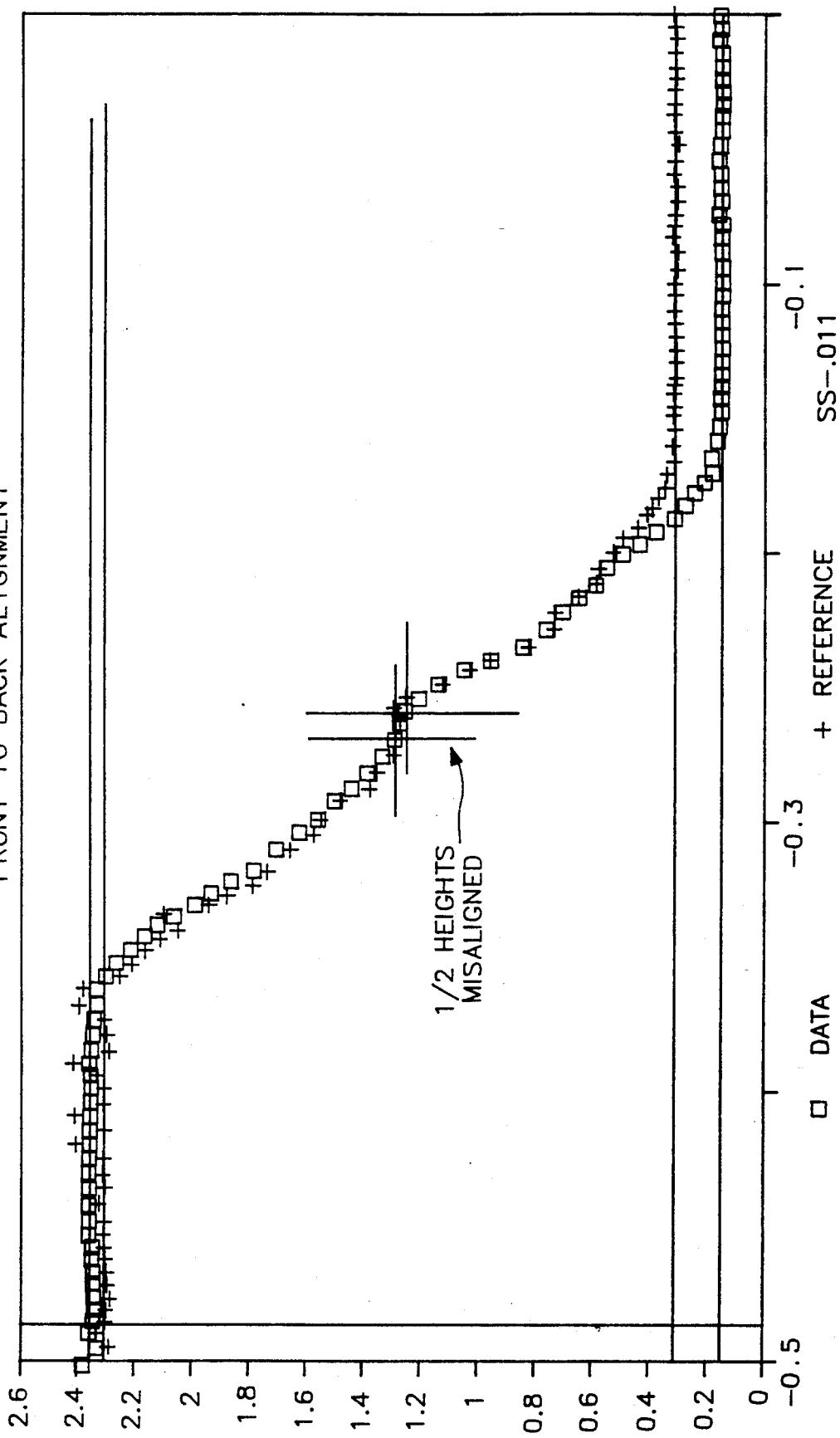

If the optical components of the detector unit or system are instead misaligned as shown in FIG. 14, the radiant energy in beam 88 will start to impinge upon one detector before it does the other. That detector will, consequently, both begin to provide an output and provide a maximum output sooner than the other detector does. As a consequence, and as is shown in FIGS. 16 and 18, the half heights of the two detectors will be misaligned — i.e., horizontally separated — along the X axis of the voltage vs. increment of withdrawal plot or graph rather than being vertically aligned (FIGS. 16 and 18).

In conjunction with the foregoing, the effects of optical misalignment can of course be compensated for by individually calibrating each detector system or unit. This, however, is expensive. The cost of calibration is instead eliminated, and interchangeability provided by employing only those optical systems determined by the novel inspection protocol just described to have accurately aligned detectors and beam splitter. The requirements for interchangeability, at least in a system employing a disposable airway adapter as shown in FIG. 1, can be satisfied if the data and reference detectors 138 and 140 and beam splitter 142 are accurately enough aligned that 90 percent of the image of beam 88 falling on these two detectors is overlapped.

Figure 19:
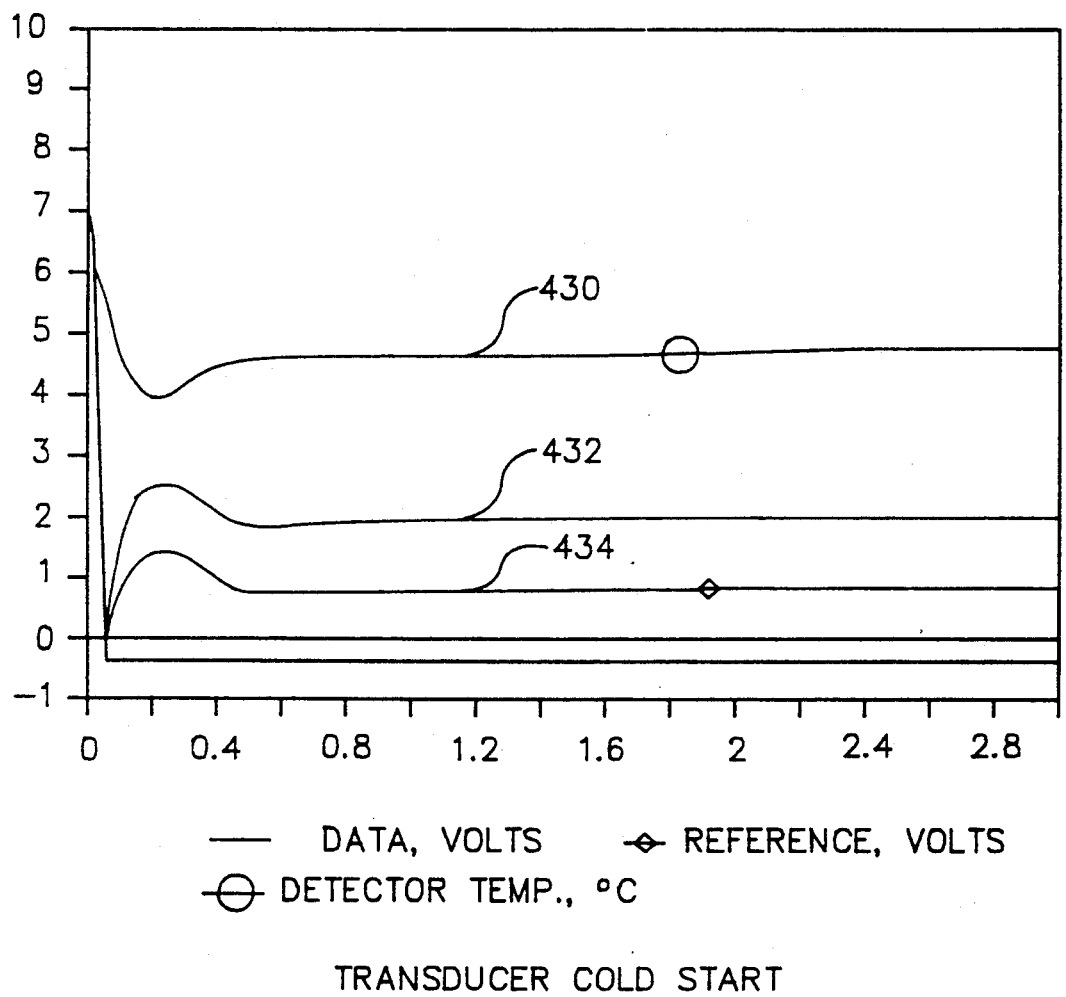
FIG. 19 is a graph showing the effect of temperature on the dark resistance output of the data and reference detectors.

It has been repeatedly pointed out above that the preferred, lead selenide-type detectors are extremely sensitive to temperature changes and that accurate gas concentration measurements therefore depend on: (a) the data and reference detectors 138 and 140 of detector unit 30 being maintained at a precisely constant temperature, and (b) the detector unit 30 being so constructed that any change in the temperature of one detector 138 or 140 will also appear in the other detector. FIG. 19 shows how the data output (detector signal level) is affected by temperature and further demonstrates that constant operating temperatures for data detector 138 and reference detector 140 can be maintained in the novel detector unit 30 disclosed herein.

Specifically, FIG. 19 shows that, as the +5 V operating voltage is applied across the data detector and reference detector heaters 144 and 146 of detector unit 30, the voltage will initially drop, then increase, and finally stabilize as the isothermal, data detector support 114 comes up to temperature. Once this occurs, the isothermal support remains at precisely the same temperature, all as shown by curve 430 in FIG. 19.

This time vs. temperature, cold start characteristic of the heater supply voltage is paralleled by the temperature vs. dark resistance output of data detector 138 and reference detector 140 shown by curves 432 and 434. As isothermal support 114 comes up to its operating temperature (typically in the range of 42°-45° C.), the dark resistance outputs of the two detectors fluctuate in response to the changing temperature of the isothermal support 114. Then, as the isothermal support stabilizes at the selected operating temperature, the dark resistance outputs of data detector 138 (curve 434) and reference detector 140 (curve 432) also stabilize at a precisely constant level. Consequently, any subsequent changes in the output levels of these two detectors can be safely attributed to the impingement thereupon of electromagnetic energy in the band transmitted by filter 176 (data detector 138) or filter 178 (reference detector 140) and not to a detector temperature change.

Once the detectors have stabilized, they are calibrated so that both have a dark resistance output of +4.5 V. As discussed above, this leads to accuracy when the data and reference detector outputs are subsequently ratioed to generate a concentration indicative signal.

Referring now to FIGS. 1, 4, and 8, it was pointed out above that the just-described transducer 24 can be employed to advantage to measure the concentration of a designated gas flowing through the sampling passage 48 in airway adapter 22. As the monitoring of the gases proceeds, and with the airway adapter 22 at ambient temperature, moisture can condense out of the surrounding environment and collect on the optical windows 60 and 62 of the airway adapter and/or the windows 76 and 78 of transducer 24. The result may be a degradation in performance and loss of accuracy.

This problem is solved simply and elegantly in accord with the principles of the present invention by maintaining the transducer housing 26 and the airway adapter 22 at an elevated temperature, preferably in the range of 42°–45° C., during the sampling process. This is accomplished with a resistance-type heater 436 mounted in a recess 438 in the casing 26 of transducer 24. Resistance heater 436 keeps casing 26 and the airway adapter 22 assembled to transducer 24 at the desired temperature.

Operation of casing heater 436 is controlled by a thermistor 440 mounted on the heater.

Plus 5 V power is supplied to case heater 436 from voltage regulator 242 in power supply 32 by way of external calibrator/connector 246 and lead 442. The opposite side of heater 436 is connected by casing heater return 444 to the return 250 from data and reference detector heaters 144 and 146.

Thermistor 440 modulates the +5 V power to control casing heater 436 and thereby keep the temperature of casing 26 and airway adapter 22 constant. The thermistor is connected in a lead 445 between voltage regulator 242 and calibrator/connector 246.

Figure 20:
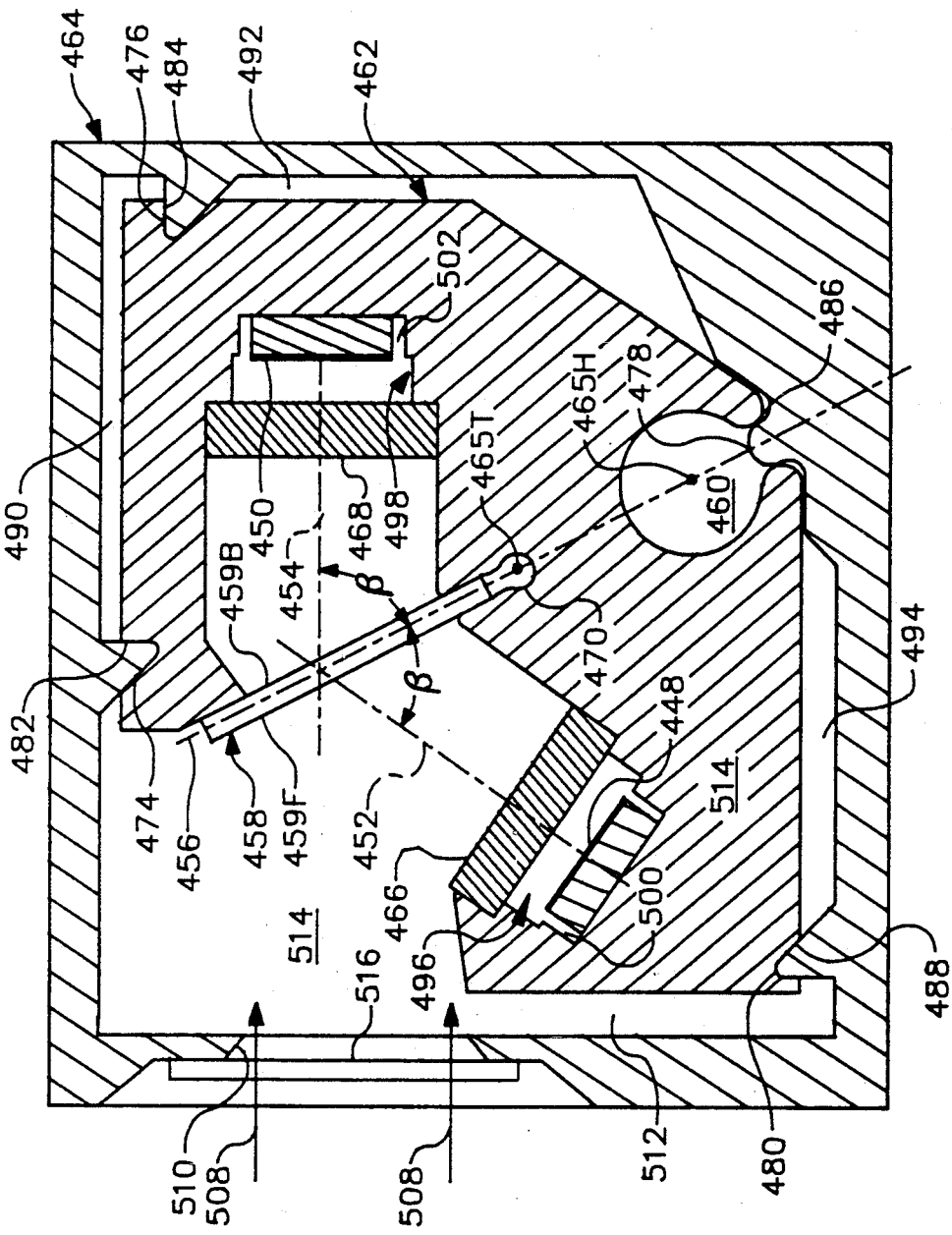
FIG. 20 is a section through a second type of detector unit embodying the principles of the present invention.

Referring still to the drawing, FIG. 20 depicts a detector unit 446 which differs from above-discussed detector unit 30 primarily in that the data and reference detectors 448 and 450 of the unit are not oriented at right angles to each other (although the angles β between the longitudinal axes of symmetry 452 and 454 of the detectors and the longitudinal midplane 456 of beam splitter 458 between front and back sides 459F and 459B are identical as they are in detector unit 30). Further, only a single, resistance-type heater 460 is employed. Also, and necessitated by these differences, is a conductive, monolithic, isothermal, detector support 462 which has a different configuration than the corresponding support 114 of detector unit 30 and a size which is reduced by making the angles β less than 90°. The internal components of detector unit 446 are housed in a detector unit case 464 differing slightly in configuration from the casing 112 of detector unit 30 with midplane 456 and the longitudinal axes 465H and 465T of detector heater 460 and thermistor 470 lying in the same plane; viz., an extension of midplane 456.

The beam splitter 458, data and reference detectors 448 and 450, bandpass filters 466 and 468, thermistor 470, and resistance heater 460 may duplicate their counterparts in detector unit 30.

The assembly of isothermal support 462 and the optical and heating system components supported from that component is retained in detector unit housing 464 in the same manner that the corresponding assembly is retained in the housing 112 of detector unit 30; viz., by integral lugs 474 . . . 480. These lugs extend inwardly from the housing and fit into complementary configured, also transversely extending recesses 482 . . . 488 in isothermal support 462. This system also accurately aligns isothermal support 462 and the components supported from it in casing 464 with heat sink providing air gaps 490, 492, and 494. These heat sinks lie between casing 464 and isothermal support 462.

The data and reference detectors 448 and 450 are supported from monolithic mount 462 in the manner discussed above in conjunction with detector unit 30; viz., in stepped recesses 496 and 498. Gaps 500 and 502 electrically isolate the electrodes of the detectors from the highly conductive, isothermal support 462.

Detector unit 446 operates in essentially the same manner that detector unit 30 does. After traversing a stream of gas(es) or other sample being analyzed, the beam of radiant energy identified by reference character 508 in FIG. 20 strikes beam splitter 458. The beam splitter resolves the energy in that beam into two moieties. One moiety contains wavelengths above a selected cutoff and the other remaining, longer wavelength energy.

The shorter wavelength energy is reflected through bandpass filter 466 onto data detector 448. The longer wavelength energy is transmitted through beam splitter 458 and bandpass filter 468 to reference detector 450. These two signals are then amplified, further processed, and combined as discussed above to produce a third signal. That signal reflects the concentration of the designated gas in the sample being analyzed.

As in detector unit 30, an aperture 510 in the front wall 512 of detector unit casing 464 allows the electromagnetic energy in beam 508 to reach the interior 514 of casing 464. An optically transparent, typically sapphire window 516 spanning this aperture keeps foreign material from reaching the interior 514 of casing 464.

Isothermal support 462 is maintained at a selected temperature by resistance heater 460 under the control of thermistor type current flow limiter 470. Control is afforded in a manner akin to that discussed about in conjunction with detector unit 30.

Aside from the components illustrated in FIG. 20, detector unit 446 will also typically include a detector unit casing heater system. For the sake of brevity, that system has not been depicted in FIG. 20 and will not be described in this text.

The invention may be embodied in many specific forms in addition to those disclosed above without departing from the spirit or essential characteristics of the invention. These embodiments are therefore to be considered in all respects as illustrative and not restrictive. The scope of the invention is instead indicated by the appended claims, and all changes which come within the meaning and range of equivalency of the claims are therefore intended to be embraced therein.

What is claimed is:

1. A transducer for non-dispersive infrared radiation gas analysis which comprises:

a detector unit which includes a detector for outputting a signal indicative of the concentration of a designated gas flowing through an airway adapter physically associated with the transducer;

means for so heating the detector as to keep it at a selected temperature and thereby eliminate detector temperature-related changes in the signal outputted by the detector;

means for heating the casing of an airway adapter associated with the transducer to a temperature high enough to keep condensation from forming and interfering with the operation of the detector; and means for independently controlling the operation of the detector heating means and the airway adapter casing heating means so that the heating of said casing will not interfere with the temperature regulating supply of power to the detector.

2. A transducer as defined in claim 1 in which the detector unit comprises:

a housing;

reference and data detectors, said data detector being the detector which outputs the signal indicative of the concentration of the designated gas; and detector supporting means for so supporting said detectors in said housing that said detectors can be maintained at the same, selected temperature, said detector supporting means comprising a monolithic, isothermal member fabricated of a material having a high coefficient of thermal conductivity.

3. A transducer as defined in claim 2 wherein the detector heating means includes means for heating both the reference and data detectors, said detector heating means including:

reference detector and data detector heaters supported from, and in conductive heat transfer relationship to, said detector supporting means; and control means for regulating the flow of current through said heaters, said control means comprising a temperature responsive, current flow limiter in conductive heat transfer relationship to said detector supporting means.

4. A transducer as defined in claim 3 in which there are heater receiving recesses in the detector supporting means of the detector unit, said recesses being configured to complement the external configurations of the data and reference detector heaters.

5. A transducer as defined in claim 3 in which the reference detector heater is proximate to the reference detector and the data detector heater is proximate to the data detector.

6. A transducer as defined in claim 3 in which the detector heating means comprises a power supply for making operating voltage and biasing voltage respectively available at selected, precise levels to said detector heaters and to the reference and data detectors.

7. A transducer as defined in claim 6 in which the power supply includes an inverter so connected that biasing voltages of opposite polarity are supplied to opposite sides of the reference detector and the data detector.

8. A transducer as defined in claim 3 in which the detector supporting means is dimensioned and configured to direct thermal energy emitted from the reference detector and data detector heaters first past the reference and data detectors, then past the temperature responsive, current flow limiter, and then overboard from the detector supporting means.

9. A transducer as defined in claim 2 which includes detector heating means for heating the reference and data detectors, said detector heating means including:

a detector heater mounted in said detector supporting means in conductive heat transfer relationship to the supporting means and in equidistantly spaced relationship to the reference and data detectors; and control means for so regulating the flow of current through the detector heater as to keep the detectors at the desired temperature, said control means comprising a temperature responsive current flow limiter in conductive heat flow relationship to the detector supporting means and in equidistantly spaced relationship to the reference and data detectors.

10. A transducer as defined in claim 2 in which the detector unit includes a beam splitting means for reflecting that energy in a beam impinging thereon and above a designated wavelength onto one of the detectors in that unit and for transmitting energy of a shorter wavelength from the same compass of the beam to the other of the detectors, said beam splitting means being supported from the detector supporting means midway between, and in mirror image relationship to, the reference and data detectors.

11. A transducer as defined in claim 10 in which:
the beam splitting means has front and back sides and a generally parallelepipedal configuration; and
the longitudinal axes of the detector heating means and the temperature responsive current limiter and the plane of symmetry between the sides of the beam splitter are in the same plane.

12. A transducer as defined in claim 2 in which:
the reference and data detectors of the detector unit have electrically conductive electrodes on their exposed surfaces;
the detector supporting means has detector receiving recesses in which the detectors are installed; and
the edges of the detector receiving recesses are spaced from the exposed surfaces to prevent shorting between the detectors and the detector supporting means.

13. A transducer as defined in claim 2 which comprises:
light trap means in the housing of the detector unit for keeping electromagnetic energy other than that making up a particular beam from reaching said reference and data detectors.

14. An transducer as defined in claim 13 in which:
the detector supporting means of the detector unit has first and second detector receiving recesses which open onto an exterior surface of the supporting means;
said reference detector and said data detector are respectively seated in said first and second recesses; and
said light trap means comprises means extending toward the axis of symmetry of the beam from said housing on those sides of the detector receiving recesses facing that aperture in the housing via which the of electromagnetic energy is admitted to interior of the housing.

15. A transducer as defined in claim 13:
which has a beam splitter for reflecting that electromagnetic energy in said beam which is above a selected wave length toward one of said detectors and for transmitting the remainder of the energy making up said beam to the other of the detectors, said beam splitter having a parallelepipedal configuration and being supported at one edge thereof from said detector supporting means; and said light trap means is configured and dimensioned to support the opposite edge of the beam splitter.

16. A transducer as defined in claim 1 which comprises:

a housing; and an electromagnetic shield in the housing of the transducer in surrounding relationship to said detector unit.

17. A transducer as defined in claim 16 in which:

the detector unit also comprises a printed circuit board assembled to said transducer housing; and said electrostatic shield comprises means operable after said shield and said detector unit have been installed in the transducer housing to make an electrical connection between the shield and the backplane of the printed circuit board.

18. A transducer as defined in claim 17 in which the electrostatic shield has side walls and means at one end of the shield for closing that end thereby completing the shielding of said detector unit/printed circuit board assembly, the means at said one end of the shield comprising foldable extensions which are integral with said side walls at said one shield end.

19. A transducer as defined in claim 16 in which:

the transducer housing has a member with top, bottom, and side walls;

said transducer housing member has internal guides for spacing the electrostatic shield from the top, bottom, and side walls of the housing and for locating the shield lengthwise in the housing; and said electrostatic shield has internal guides for positioning a detector unit in the shield.

20. A transducer as defined in claim 19 in which the housing also comprises:

first and second end closures configured to complement the housing member;

a seal between the housing member and each of the end closures; and means for retaining the end closures, the seals, and the housing member in assembled relationship with the electrostatic shield and the detector unit installed therein, said retaining means comprising a fastener extending from the first end closure through that end closure and the housing member to the second end closure.

21. A transducer as defined in claim 1 in which:

said detector unit comprises: a printed circuit board; a housing mounted on the printed circuit board; and a support in said housing, said detector, said detector heating means, and a temperature responsive current flow limiter being integrated with said support in conductive heat transfer relationship thereto; and said printed circuit board has circuits for connecting said detector and said detector heating means to a power supply and for connecting the current flow limiter in controlling relationships to the power supply and the detector heating means.

22. A transducer as defined in claim 21 wherein:

said detector unit comprises a reference detector and a data detector;

the detector heating means comprises a reference detector heater and a data detector heater; and the printed circuit board has circuits for connecting the reference and data detectors to the power supply and for connecting the temperature responsive current flow limiter to the power supply.

23. A transducer for non-dispersive electromagnetic radiation gas analysis which comprises:

a housing;

an electromagnetic energy detector unit in said housing; and an electrostatic shield in said housing in surrounding relationship to said detector unit;

the detector unit comprising detector means in said housing and a printed circuit board assembled to said housing; and said electrostatic shield comprising means operable after said shield and said detector unit have been installed in the transducer housing to make an electrical connection between the shield and the backplane of the printed circuit board.

24. A transducer as defined in claim 23 in which the electrostatic shield has side walls and means at one end of the shield for closing that end and thereby completing the shielding of said detector unit/printed circuit board assembly, the means at said one end of the shield comprising foldable extensions which are integral with said side walls at said one shield end.

* * * * *